(12) United States Patent
Ishikawa

(10) Patent No.: US 7,172,612 B2
(45) Date of Patent: Feb. 6, 2007

(54) TROCAR AND TROCAR SYSTEM

(75) Inventor: Manabu Ishikawa, Akiruno (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 10/218,081

(22) Filed: Aug. 12, 2002

(65) Prior Publication Data
US 2003/0004528 A1 Jan. 2, 2003

Related U.S. Application Data

(63) Continuation of application No. PCT/JP01/10795, filed on Dec. 10, 2001.

(30) Foreign Application Priority Data

Dec. 12, 2000 (JP) ............................ 2000-377866
Jun. 28, 2001 (JP) ............................ 2001-196587

(51) Int. Cl.
*A61B 17/34* (2006.01)
(52) U.S. Cl. ..................... 606/185; 606/169
(58) Field of Classification Search ............... 606/169, 606/185, 191; 604/164.1, 164.01
See application file for complete search history.

(56) References Cited

U.S. PATENT DOCUMENTS

| | | | |
|---|---|---|---|
| 4,535,759 A | * | 8/1985 | Polk et al. ..................... 601/2 |
| 4,981,482 A | * | 1/1991 | Ichikawa ..................... 606/108 |
| 4,994,027 A | * | 2/1991 | Farrell ......................... 604/510 |
| 5,746,720 A | * | 5/1998 | Stouder, Jr. ................. 604/117 |

FOREIGN PATENT DOCUMENTS

| | | |
|---|---|---|
| JP | 5-44291 | 7/1993 |
| JP | 7-51281 | 2/1995 |
| JP | 9-489 | 1/1997 |
| JP | 2000-229085 | 8/2000 |

OTHER PUBLICATIONS

English translation of Japanese Office Action dated Nov. 15, 2005 issued in connection with corresponding application No. 2001-196587.
Untranslated copy of Japanese Office Action dated Nov. 15, 2005 issued in connection with corresponding application No. 2001-196587.
English translation of Japanese Office Action dated Jul. 18, 2006 issued in connection with corresponding application No. 2000-377866.
Untranslated copy of Japanese Office Action dated Jul. 18, 2006 issued in connectino with corresponding No. 2000-377866.
English translation of Japanese Office Action dated Jun. 13, 2006 issued in connection with corresponding application No. 2001-196587.
Untranslated copy of Japanese Office Action dated Jun. 13, 2006 issued in connection with corresponding application No. 2001-196587.

* cited by examiner

*Primary Examiner*—Michael Thaler
(74) *Attorney, Agent, or Firm*—Ostrolenk, Faber, Gerb & Soffen, LLP

(57) ABSTRACT

A trocar has a projection portion which is a part of a tube projecting from a distal end portion of an outer tube in the state in which the tube is inserted in the outer tube, an amount of projection of the projection portion from the distal end portion of the outer tube varying in accordance with relative movement of the tube and the outer tube.

27 Claims, 25 Drawing Sheets

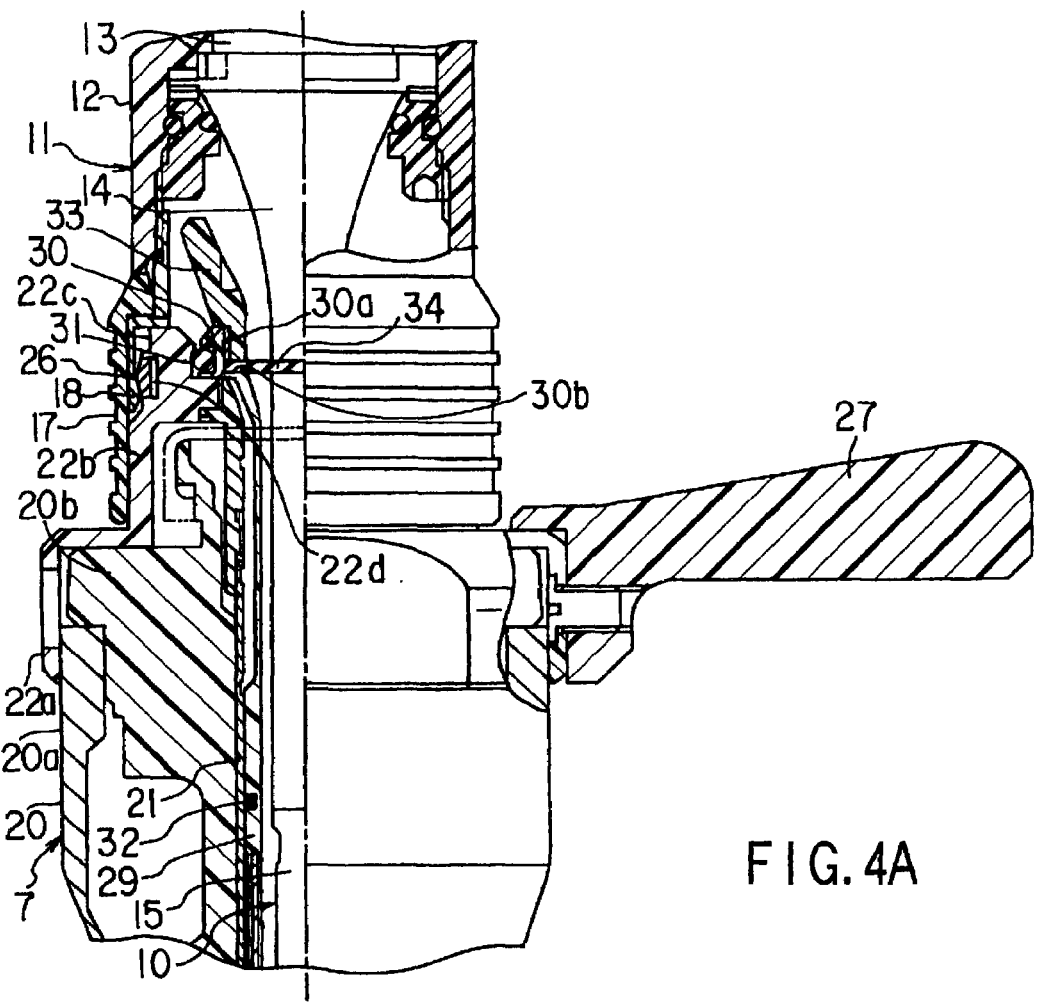
FIG. 4A
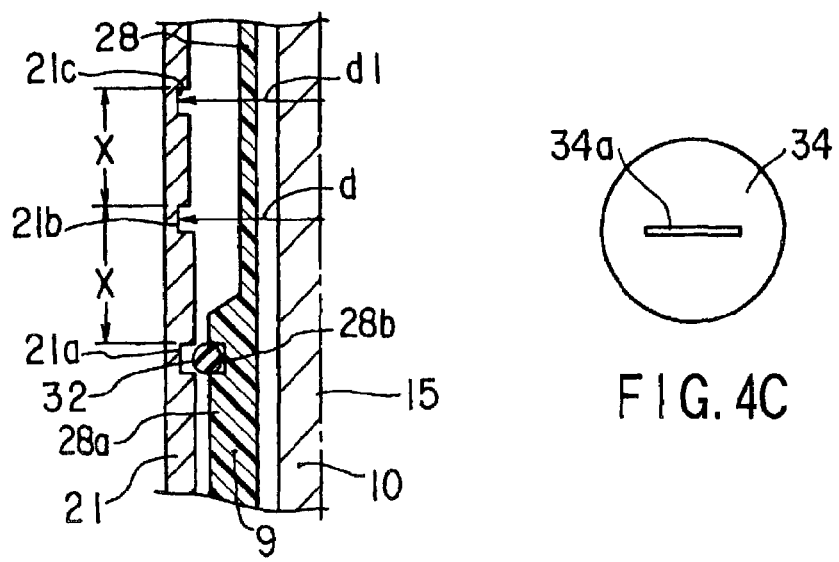
FIG. 4B
FIG. 4C

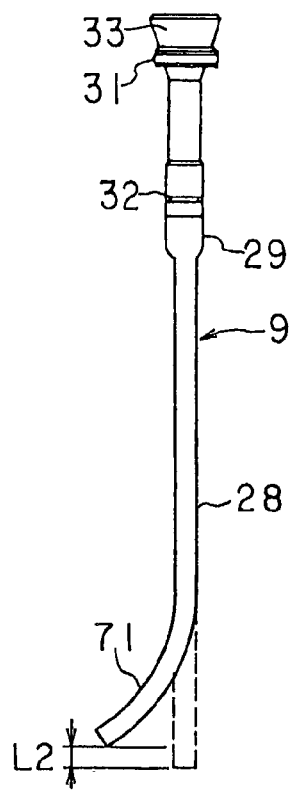 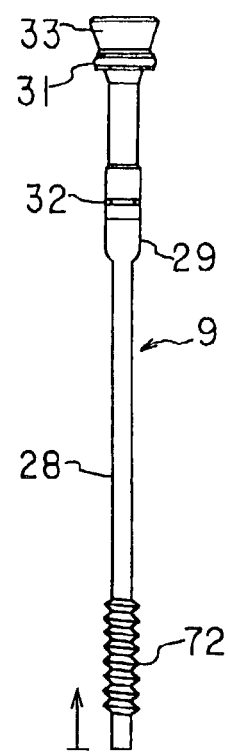 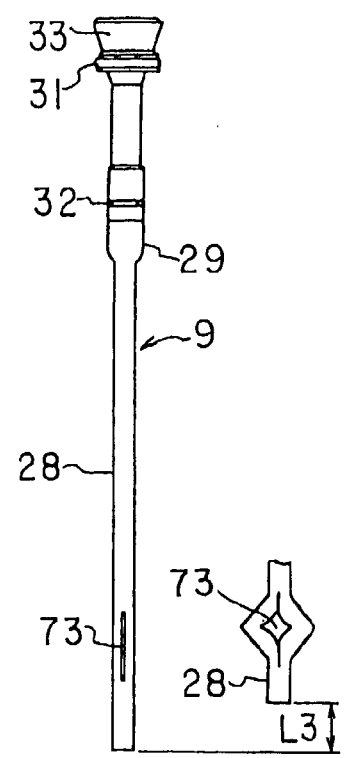
F I G. 12A          F I G. 12B          F I G. 12C
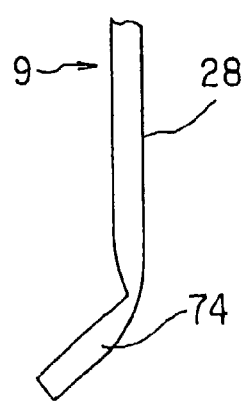 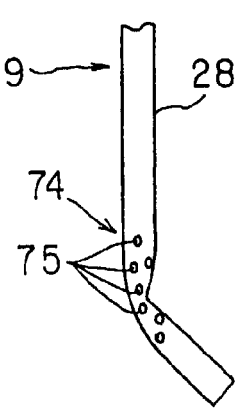
F I G. 13A          F I G. 13B

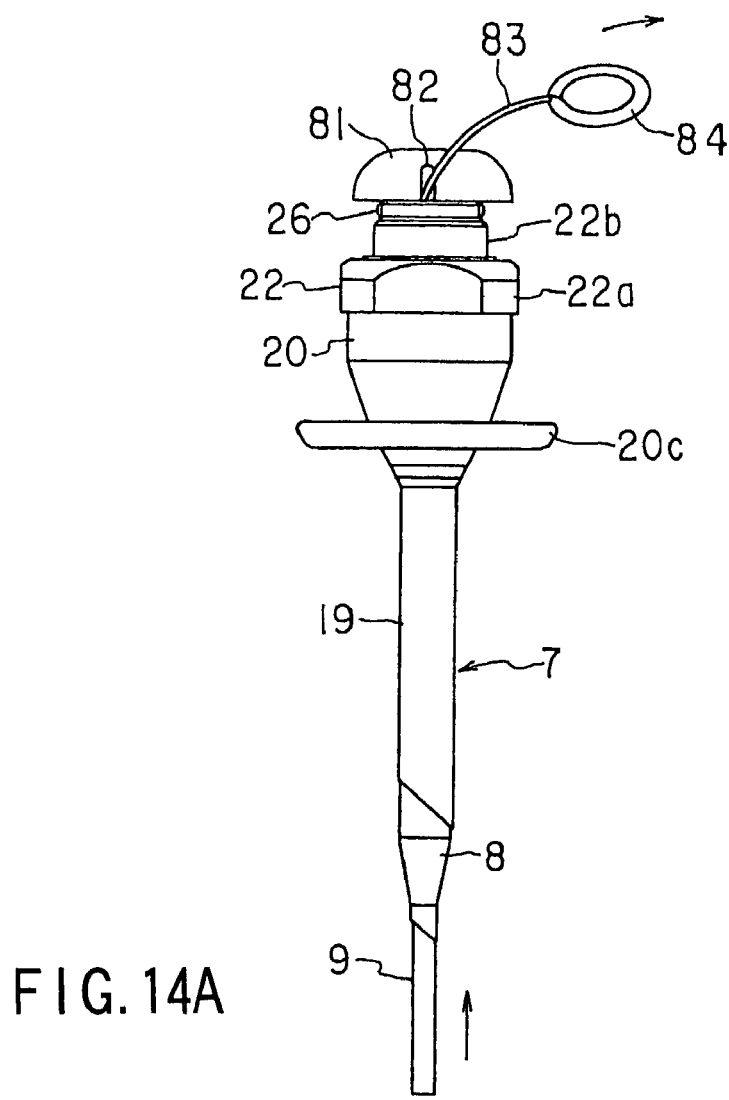
FIG. 14A
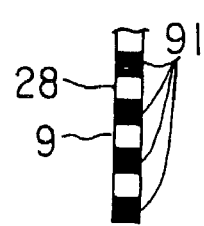 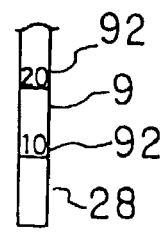
FIG. 14B   FIG. 14C

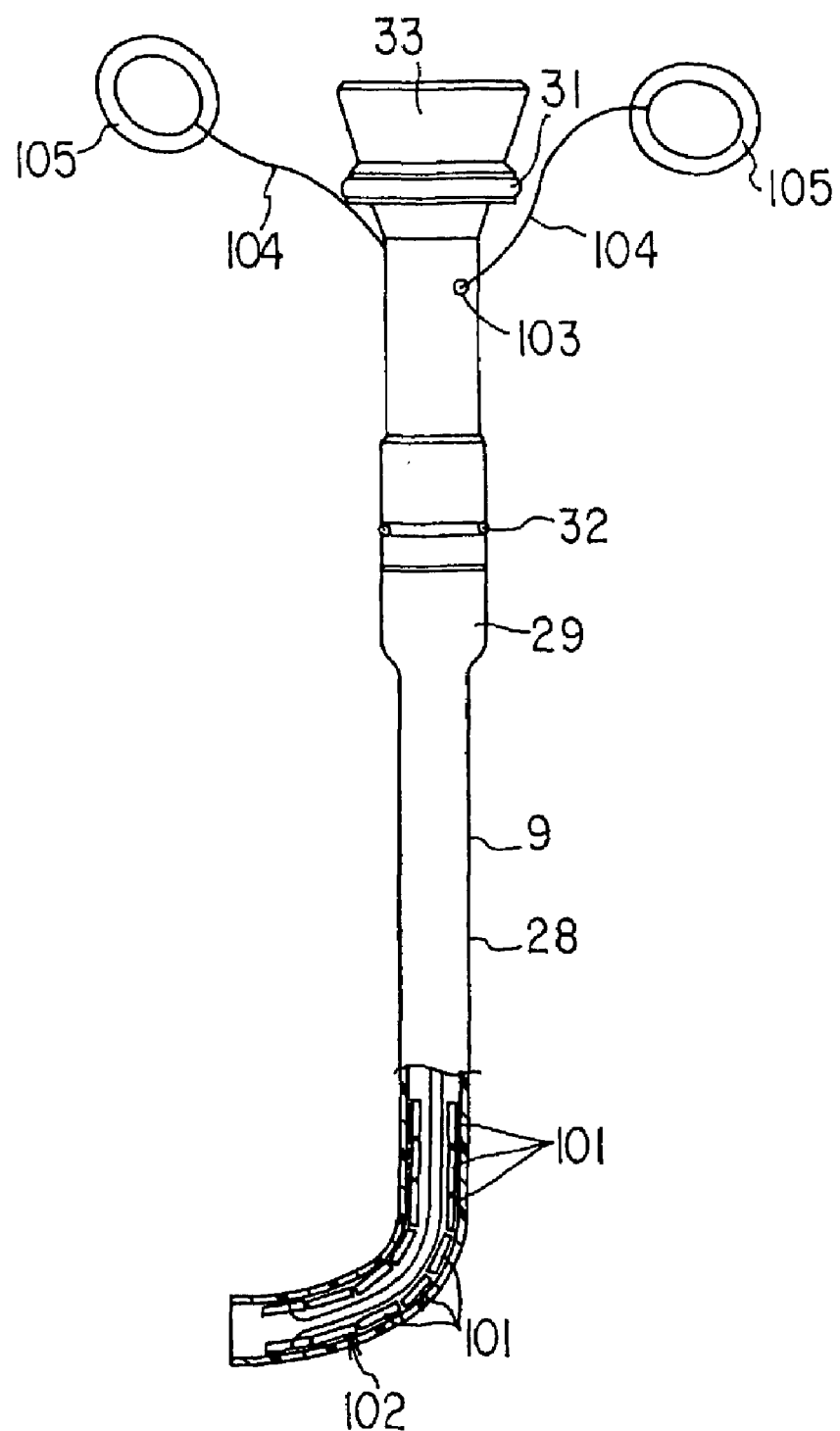
F I G. 15

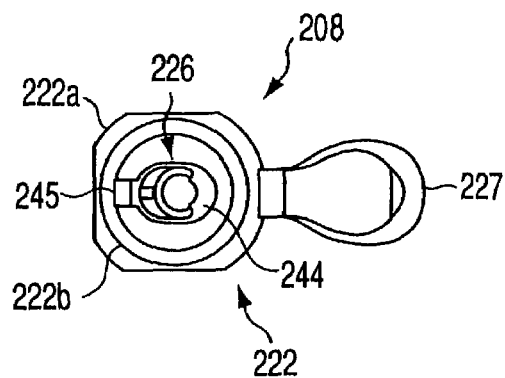
F I G. 20A
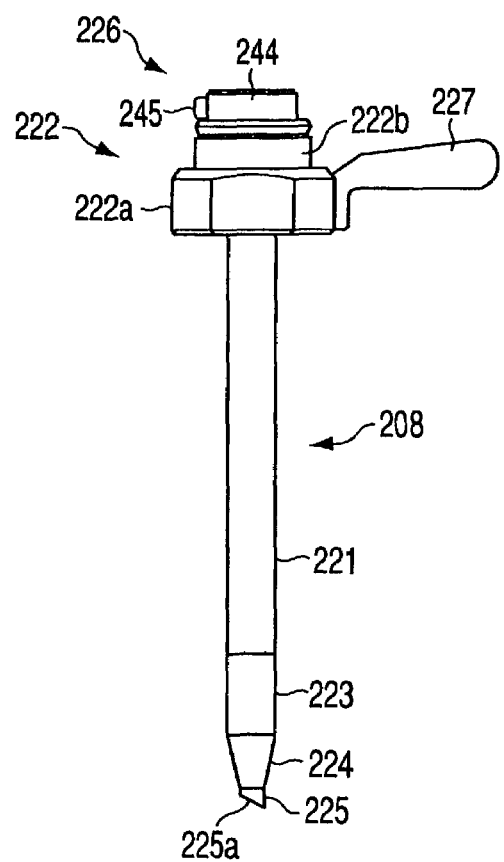
F I G. 20B

TROCAR AND TROCAR SYSTEM

CROSS-REFERENCE TO RELATED APPLICATIONS

This is a Continuation Application of PCT Application No. PCT/JP01/10795, filed Dec. 10, 2001, which was not published under PCT Article 21 (2) in English.

This application is based upon and claims the benefit of priority from the prior Japanese Patent Applications No. 2000-377866, filed Dec. 12, 2000; and No. 2001-196587, file Jun. 28, 2001, the entire contents of both of which are incorporated herein by reference.

BACKGROUND OF THE INVENTION

1. Field of the Invention

The present invention relates to a trocar and a trocar system, wherein a trocar tube, which is to be inserted in a patient's body and used as a guide tube for an instrument inserted in the body cavity, is made to stay in a state in which the tube has pierced and penetrated the patient's skin and body wall.

2. Description of the Related Art

In general, in the prior art, there is used a trocar apparatus wherein a trocar tube, which is to be inserted in a patient's body and used as a guide tube for an instrument inserted in the body cavity, is made to stay in a state in which the tube has pierced and penetrated the patient's skin and body wall. In the trocar apparatus, a trocar needle having a pointed pierce needle at its distal end is detachably combined with a tube having an insertion portion to be inserted in a patient.

When the trocar apparatus is to be used, the trocar needle and the tube are integrally combined in advance. In this state, the tip end of the trocar needle is made to pierce the patient's skin, and the trocar needle and tube are made to pierce the body wall and are inserted in the body cavity. Further, after the trocar has been inserted in the body cavity, the trocar needle is drawn out of the tube and thus the tube is made to stay in the body wall. Thereby, the tube can be used as a guide tube for an optical scope or an instrument for observation and treatment of a diseased part.

Jpn. Pat. Appln. KOKOKU Publication No. 5-57863, for instance, discloses an apparatus for inserting a trocar into the body cavity using ultrasonic oscillation. In the state in which a trocar needle and a tube are integrally combined, ultrasonic oscillation is transmitted to the trocar needle. The trocar needle, while being oscillated by ultrasonic waves, is made to pierce the patient's skin and body wall. In this case, by virtue of ultrasonic oscillation, the trocar can safely be made to pierce, and inserted in, the patient's body wall with a relatively weak force. Thus, the tube for guiding the instrument for treatment, etc. is inserted and made to stay in the body wall.

Jpn. Pat. Appln. KOKAI Publication No. 11-89851 shows an ultrasonic trocar system with different construction. In this system, a substantially conical, tapered adapter is provided between a trocar needle with a relatively small outside diameter and a tube. The small-diameter trocar needle is used when the trocar is inserted. Thereby, the diameter of the pierce hole made by the trocar needle in the patient's body wall is decreased and the degree of invasion on the patient is reduced. Further, the tapered adapter is inserted in the pierce hole made in the body wall. The tapered adapter increases the diameter of the pierce hole made in the body wall by the trocar needle up to the outside diameter of the tube. Accordingly, the large-diameter tube can smoothly be inserted in the pierce hole in the patient's body wall.

When the trocar needle, which is being oscillated by ultrasonic, is made to pierce the patient's skin and body wall, as disclosed in Jpn. Pat. Appln. KOKOKU Publication No. 5-57863, heat may affect the living tissue due to contact with the trocar needle that is being oscillated by ultrasonic. In order to minimize the invasion on the living tissue when the trocar needle is made to pierce the body wall, it is necessary to make the trocar needle pierce the body wall within a minimum possible time period by using the trocar needle with a relatively small outside diameter.

In the apparatus of Jpn. Pat. Appln. KOKAI Publication No. 11-89851, the diameter of a small-diameter pierce hole is increased by a conical portion of a tapered adapter up to a relatively large outside diameter of the tube. Thus, the axial length of that portion of the tapered adapter, which projects from the distal end of the tube, is relatively long. Where the distal projecting portion of the tapered adapter is long, it is possible that while the diameter of the pierce hole is being increased by the adapter, the distal end of the adapter may come in contact with, and press, an organ in the abdominal cavity. It is thus desirable that the distal projecting portion of the adapter be made as short as possible.

On the other hand, where the distal projecting portion of the adapter is short, it is possible that when the adapter is inserted in the pierce hole in the patient's body wall, it may not pierce the abdominal wall. In such a case, a time-consuming work is required. For example, the adapter used during the treatment has to be replaced with another adapter having a longer distal projecting portion. As a result, the time of work for inserting the tube in the body wall and staying it therein will increase.

In the conventional trocar apparatus, the proximal end portion of the trocar needle is engaged with the proximal end portion of the tube with a relatively weak force by means of a resilient ring such as a C-ring. Consequently, when the trocar needle is made to piece the patient's body wall, the engagement between the proximal end portion of the tube and the proximal end portion of the trocar needle may be released if the user holds the trocar apparatus at an undesirable position. As a result, the operation of the trocar apparatus becomes unstable.

Moreover, the length of the distal projecting portion of the trocar needle, which projects from the distal end of the tube, is fixed at a predetermined value. While the trocar needle is being made to pierce the patient's body wall, the amount of insertion of the distal end portion of the trocar needle is determined by the sense of the finger, the experience, etc. in accordance with conditions such as the thickness of the body wall or the location of piercing. This work is difficult and time-consuming.

The present invention has been made in consideration of the above circumstances. An object of the invention is to provide a trocar system wherein when a small-diameter pierce hole made by a trocar needle is increased up to an outside diameter of a tube, an organ in the abdominal cavity, for instance, is not pressed and the tube can easily and quickly be inserted and stayed in the body wall.

Another object of the invention is to provide a trocar system wherein when a small-diameter pierce hole made by a trocar needle is increased up to an outside diameter of a tube, an organ in the abdominal cavity, for instance, is not pressed and the tube can easily and quickly be inserted and stayed in the body wall, and also the work for inserting a distal end portion of the trocar needle can be easily and stably performed.

BRIEF SUMMARY OF THE INVENTION

A trocar according to the present invention comprises:
a needle which is pierceable into a body wall;
a tube in which the needle is insertable;
an outer tube in which the tube is insertable and which is movable relative to the tube in the state in which the tube is inserted in the outer tube; and
a projection portion which is a part of the tube projecting from a distal end portion of the outer tube in the state in which the tube is inserted in the outer tube, an amount of projection of the projection portion from the distal end portion of the outer tube varying in accordance with relative movement of the tube and the outer tube.

In this invention, the amount of projection of the projection portion of the tube, which projects from the distal end of the outer tube, is adjusted. Accordingly, the amount of projection of the projection portion of the tube can be desirably adjusted in accordance with conditions such as the thickness of the body wall for piercing, or the distance from the organ in the body.

A trocar system according to the invention comprises:
a trocar needle which is made to pierce a body wall;
an outer tube in which the trocar needle is inserted;
a dilator which is interposed between the outer tube and the trocar needle and has a pierce hole expansion portion that dilates a small-diameter pierce hole made by the trocar needle; and
a guide member which includes a cylindrical portion projecting outward from a distal end portion of the dilator and is attached to the dilator such that an amount of projection of the cylindrical portion can be varied.

In this invention, the amount of projection of the distal end portion of the guide member, which projects outward from the distal end of the dilator interposed between the outer tube and the trocar needle, is adjusted. Accordingly, the amount of projection of the distal end portion of the guide member can be desirably adjusted in accordance with conditions such as the thickness of the body wall for piercing, or the distance from the organ in the body.

A trocar according to the invention comprises:
a trocar needle which is made to pierce a body wall;
an outer tube in which the trocar needle is inserted;
a dilator which is interposed between the outer tube and the trocar needle and has a pierce hole expansion portion that dilates a small-diameter pierce hole made by the trocar needle; and
a cylindrical member projecting outward from a distal end portion of the dilator,
wherein a guide member, which is supported to be axially movable relative to the dilator and guides insertion of the dilator, is optionally combined in use, and
there is provided an adjusting mechanism for adjusting a position of a distal end portion of the needle projecting from the outer tube.

In this invention, the amount of projection of the distal end portion of the guide member, which projects outward from the distal end of the dilator interposed between the outer tube and the trocar needle, is adjusted. Thereby, the amount of projection of the distal end portion of the guide member can be desirably adjusted in accordance with conditions such as the thickness of the body wall for piercing, or the distance from the organ in the body. Furthermore, the position of the distal end portion of the needle, which projects from the outer tube, is adjusted in advance by the adjusting mechanism prior to the insertion in the body wall. Thereby, the amount of projection of the distal end portion of the needle projecting from the dilator can be desirably adjusted in accordance with conditions such as the thickness of the body wall for piercing, or the location for piercing.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4A is a partial cross-sectional side view showing an internal structure of the assembled unit of the handpiece unit of the ultrasonic trocar according to the first embodiment;

FIG. 4B is a vertical cross-sectional view showing a click mechanism provided between the dilator and the guide member;

FIG. 4C is a plan view showing a seal sheet;

FIG. 12A is a side view showing a main part of a fourth modification of the guide member of the first embodiment;

FIG. 12B is a side view showing a main part of a fifth modification of the guide member of the first embodiment;

FIG. 12C is a side view showing a main part of a sixth modification of the guide member of the first embodiment;

FIG. 13A is a side view showing a main part of a seventh modification of the guide member of the first embodiment;

FIG. 13B is a side view showing a main part of an eighth modification of the guide member of the first embodiment;

FIG. 14A is a side view showing a handpiece unit, in its assembled state, of an ultrasonic trocar in a trocar system according to a fourth embodiment of the invention;

FIG. 14B is a side view showing an example of an indication section provided at a distal end portion of the guide member;

FIG. 14C is a side view showing another example of the indication section provided at the distal end portion of the guide member;

FIG. 15 is a partial cross-sectional side view of a bending portion of the guide member in a trocar system according to a fifth embodiment of the invention;

FIG. 20A is a plan view showing the positional relationship between the direction of the handle of the dilator and lock button in the ultrasonic trocar of the sixth embodiment;

FIG. 20B is a side view of the dilator;

DETAILED DESCRIPTION OF THE INVENTION

Figure 1:
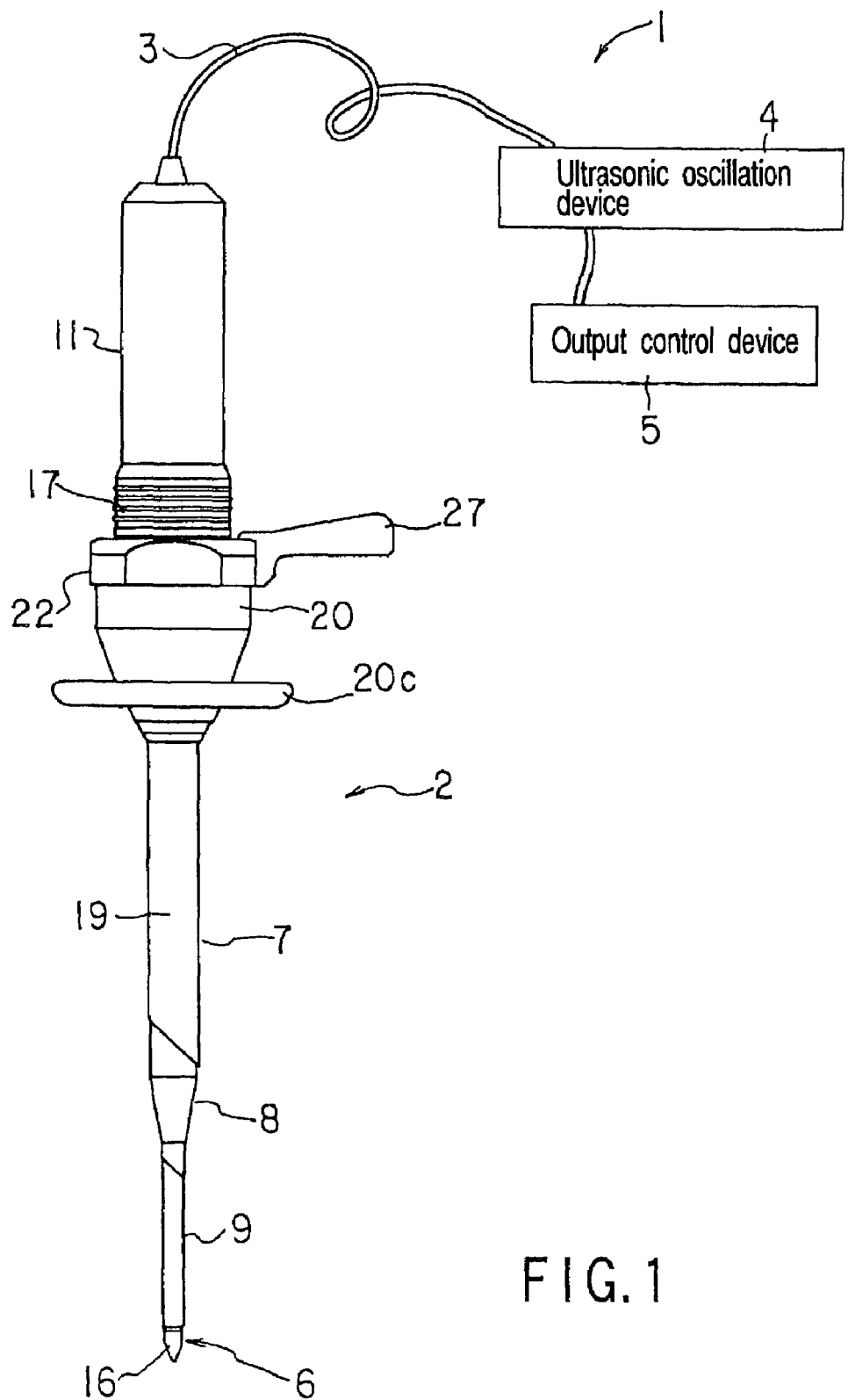
FIG. 1 is a side view of a handpiece unit, in its assembled state, of an ultrasonic trocar in a trocar system according to a first embodiment of the present invention.

A first embodiment of the present invention will now be described with reference to FIGS. 1 to 6B. FIG. 1 schematically shows the entire structure of a trocar system 1 according to this embodiment. This trocar system 1 is provided with a handpiece unit 2 of an ultrasonic trocar, which is held and operated by the operator. The handpiece unit 2 is connected to an ultrasonic oscillation device 4 over a connection cable 3. The ultrasonic oscillation device 4 supplies energy for ultrasonic oscillation. The ultrasonic oscillation device 4 is connected to an output control device 5, such as a foot switch or a hand switch, for controlling energy output.

The handpiece unit 2 of the ultrasonic trocar comprises a trocar needle 6 for piercing into the body wall; a tube 7 in which the trocar needle 6 is inserted; a dilator 8 inserted between the tube 7 and trocar needle 6; and a guide member 9 formed of a soft cylindrical member and inserted in the dilator 8. The guide member 9 may be formed of a hard member. The handpiece unit 2 of the ultrasonic trocar of this embodiment is selectively used in two modes: an assembled mode in which the trocar needle 6, tube 7, dilator 8 and guide member 9 are combined, and a disassembled mode in which these elements are separated. FIG. 1 shows a state in which the trocar needle 6, tube 7, dilator 8 and guide member 9 are combined.

Figure 3:
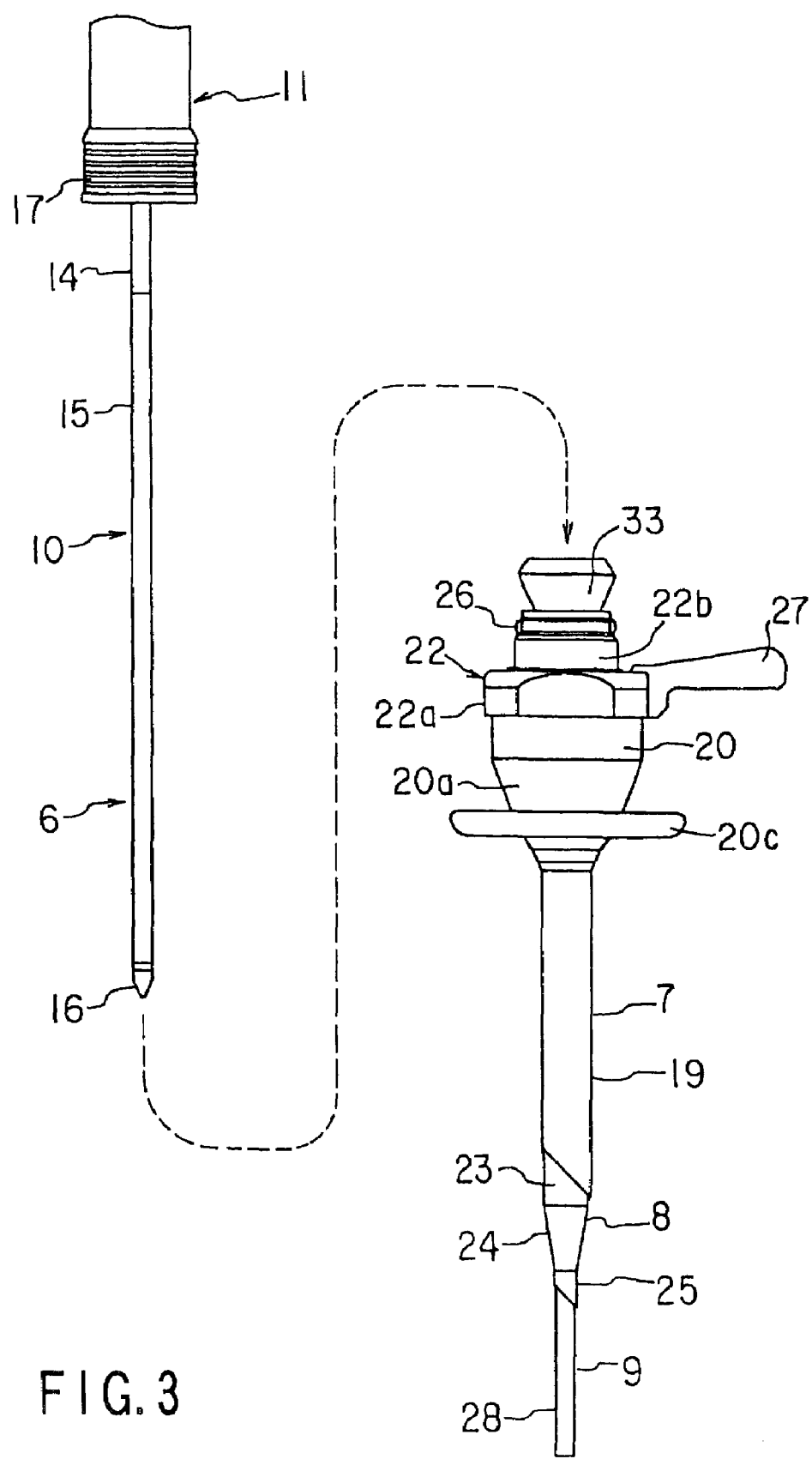
FIG. 3 is a side view showing an assembled unit of the trocar tube, dilator and guide member, and a trocar needle, of the ultrasonic trocar according to the first embodiment.

The trocar needle 6 is provided with a substantially straight probe 10, as shown in FIG. 3. A proximal-side handle 11 is disposed at a proximal end portion of the probe 10. The proximal-side handle 11 is provided with a substantially cylindrical housing 12, as shown in FIG. 4A.

The housing 12 of the trocar needle 6 includes an ultrasonic oscillation element 13 that is an element for producing ultrasonic oscillation. A horn 14 for amplifying ultrasonic oscillation is disposed at a distal end portion of the ultrasonic oscillation element 13. A distal end portion of the horn 14 extends forward from the end of the housing 12. The distal end portion of the horn 14 is detachably screwed to a proximal end portion of an ultrasonic oscillation transmission rod (oscillation transmission rod) 15. A distal end of the oscillation transmission rod 15 is provided with a tapered pierce needle (needle body) 16. The pierce needle 16 is tapered, for example, in a conical shape, a trigonal pyramidal shape or a quadrangular pyramidal shape. Thereby, mechanical oscillation of the ultrasonic oscillation element 13 is transmitted to the distal-end pierce needle 16 provided at the distal end of the ultrasonic oscillation transmission rod 15.

A cylindrical connection member 17 is provided at the distal side of the housing 12. A C-ring receiving portion 18 extending inward is formed on the inner periphery of the connection member 17.

Figure 2:
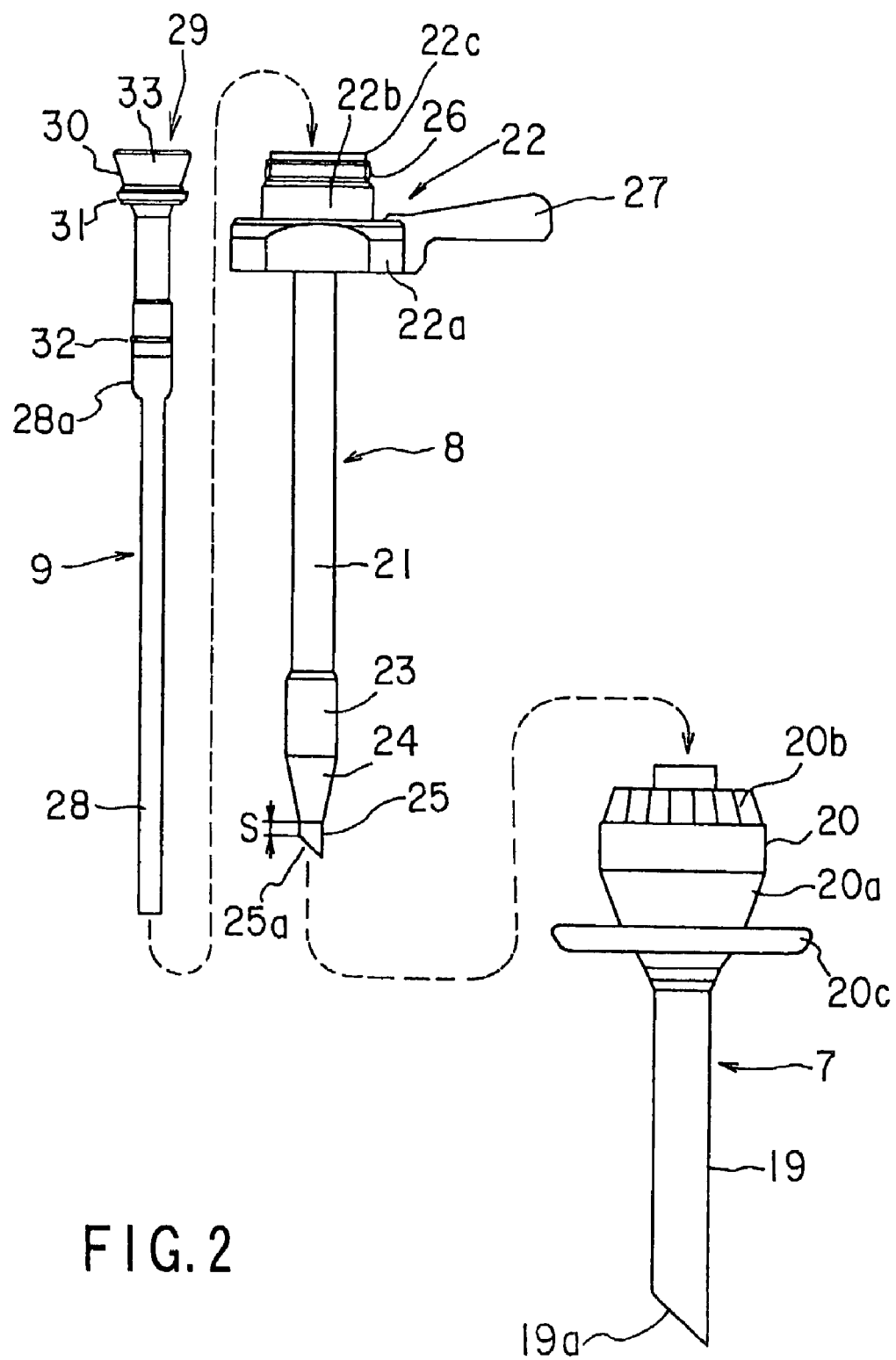
FIG. 2 is a side view showing a trocar tube, a dilator and a guide member of the ultrasonic trocar of the first embodiment.

As is shown in FIG. 2, the trocar tube 7 has a tubular insertion portion 19 with a relatively large diameter (e.g. about 13 mm). A proximal end portion 20 is provided at a proximal end of the insertion portion 19.

A distal end portion of the insertion portion 19 has a distal bevel face 19a. The distal bevel face 19a is inclined to a direction perpendicular to the center axis of the insertion portion 19.

The proximal end portion 20 has a large-diameter cylindrical portion 20a. An insertion guide member 20b is engaged with an opening end portion of the large-diameter cylindrical portion 20a. A substantially flange-shaped finger hook portion 20c is formed on the outer periphery of the large-diameter cylindrical portion 20a. The insertion guide member 20b is provided with a seal member such as a valve (not shown). When an insertion instrument is inserted in the tube 7, the seal member effects sealing within the tube.

The dilator 8 has a tubular insertion portion 21. A proximal end portion 22 is provided at a proximal end of the insertion portion 21. A large-diameter distal straight portion 23 for alignment is provided at a distal end of the insertion portion 21. The outside diameter of the distal straight portion 23 is set to be substantially equal to the inside diameter of the insertion portion 19 of tube 7. A distal end portion of the distal straight portion 23 is provided with a pierce hole expansion portion 24 having a substantially conical tapered shape.

A conical distal end portion of the pierce hole expansion portion 24 is provided with a straight breakage-prevention portion 25. A length S of the breakage-prevention portion 25 is set at a predetermined value, as measured from the conical distal end of the pierce hole expansion portion 24. A distal end portion of the breakage-prevention portion 25 is provided with a distal bevel face 25a. The distal bevel face 25a is inclined to a direction perpendicular to the center axis of the insertion portion 21.

As is shown in FIG. 4A, the proximal end portion 22 of dilator 8 includes a large-diameter cylindrical portion 22a and a small-diameter cylindrical portion 22b having a smaller diameter than the cylindrical portion 22a. The inside diameter of the large-diameter cylindrical portion 22a is set to be substantially equal to the outside diameter of the large-diameter cylindrical portion 20a of trocar tube 7. The outside diameter of the small-diameter cylindrical portion 22b is set to be substantially equal to the inside diameter of the connection member 17 of handle 11. When the dilator 8 and trocar tube 7 are coupled, the large-diameter cylindrical portion 22a of dilator 8 is detachably fitted on the vicinity of the opening end of the large-diameter cylindrical portion 20a of trocar tube 7.

A small-diameter connection cylindrical portion 22c is formed on an outer periphery of a distal end portion of the small-diameter cylindrical portion 22b of dilator 8. An annular C-ring receiving groove 22d is formed in an outer periphery of the connection cylindrical portion 22c. A C-ring 26 for engaging the trocar needle 6 is fitted in the C-ring receiving groove 22d. The C-ring 26 is disposed at a position corresponding to the C-ring receiving portion 18 of connection member 17 of trocar needle 6. When the trocar needle 6 and dilator 8 are to be coupled, the connection member 17 of housing 12 of trocar needle 6 is fitted on the small-diameter cylindrical portion 22b of dilator 8. In this case, the C-ring 26 of dilator 8 is detachably engaged in the C-ring receiving portion 18 of trocar needle 6. A proximal end portion of an operation handle 27 is screwed to the outer periphery of the large-diameter cylindrical portion 22a of dilator 8.

As is shown in FIG. 2, the guide member 9 has a thin straight portion 28. A proximal end portion of the straight portion 28 is provided with a handle section 29. The straight portion 28 is formed of, e.g. Teflon (trademark): PTFE (polytetrafluoroethylene), which is a soft resin material with high heat resistance and smoothness. The straight portion 28 is put in contact with the probe that is oscillated by ultrasonic. For example, even when an inner peripheral surface of a hard metallic pipe is coated with Teflon to form a straight portion 28, the same advantage is obtained as with the resin-made straight portion 28.

The inside diameter of the straight portion 28 is set to be substantially equal to the outside diameter of the pierce needle 16 of trocar needle 6. A proximal end portion of the straight portion 28 is provided with an alignment portion 28a having a diameter substantially equal to the inside diameter of the insertion portion 21 of dilator 8.

A large-diameter seal receiving ring 30 is formed at the proximal end portion of the straight portion 28. An annular O-ring receiving groove 30a is formed in the outer periphery of seal receiving ring 30. A first O-ring 31 is fitted in the O-ring receiving groove 30a. When the guide member 9 is inserted in the dilator 8 for assembly, the first O-ring 31 of guide member 9 is put in pressure contact with the inner periphery of the connection cylindrical portion 22c of dilator 8. Thereby, seal is effected between the seal receiving ring 30 of guide member 9 and the connection cylindrical portion 22c of dilator 8.

Furthermore, as shown in FIG. 4B, an annular O-ring receiving groove 28b is formed in the outer periphery of the alignment portion 28a of straight portion 28. A second O-ring 32 is fitted in the O-ring receiving groove 28b. When the guide member 9 is inserted in the dilator 8 for assembly, the second O-ring 32 of guide member 9 is put in pressure contact with the inner periphery of the insertion portion 21 of dilator. Thereby, seal is effected between the outer periphery of the alignment portion 28a of guide member 9 and the inner periphery of the insertion portion 21 of dilator 8.

A plurality (three in the embodiment) of O-ring engagement grooves 21a, 21b and 21c are formed in the inner periphery of the insertion portion of dilator 8. The O-ring engagement grooves 21a, 21b and 21c are provided in the direction of insertion of the guide member 9. The interval between O-ring engagement grooves 21a and 21b and the interval between O-ring engagement grooves 21b and 21c are set at about 10 mm, respectively. When the guide member 9 is drawn out of the insertion portion 21 of dilator 8, the second O-ring 32 of guide member 9 is detachably engaged with the O-ring engagement grooves 21a, 21b and 21c in succession. Thus, when the guide member 9 is drawn out of the insertion portion 21 of dilator 8, the user can sense a click and recognize the amount of draw-out of the guide member 9 without observation by the naked eye.

The O-ring engagement groove 21c is disposed at that area of the insertion portion 21 of dilator 8, which corresponds to the final position in the draw-out direction of the guide member 9. A diameter d1 of this O-ring engagement groove 21c is less than a diameter d of each of the other O-ring engagement grooves 21a and 21b (d1<d). Thus, the O-ring engagement groove 21c is formed to have the least depth.

As a result, when the guide member 9 is drawn out of the insertion portion 21 of dilator 8, the intensity of operational sensation, i.e. the sensation of engagement, which is felt when the second O-ring 32 of guide member 9 is engaged with the O-ring engagement groove 21c, is made greater than that obtained when the second O-ring 32 is engaged with the other O-ring engagement grooves 21a, 21b. Thereby, the draw-out position of the guide member 9 can be recognized more exactly by sensation. This also prevents unintentional draw-out of the guide member.

The handle section 29 of guide member 9 includes a handle portion 33. The handle portion 33 is formed to have a substantially truncated-conical cross section. As is shown in FIG. 4A, a small-diameter end portion of the handle portion 33 is screwed to the inner periphery of the seal receiving ring 30. A tapered outer periphery of the handle portion 33 is subject to non-slip treatment (not shown).

The inner periphery of the seal receiving ring 30 is provided with a stepped seal receiving portion 30b. As is shown in FIG. 4C, a circular air-tight seal member 34 is disposed at the seal receiving portion 30b. The seal member 34 is, e.g. a rubber sheet. The seal member 34 is clamped and fixed between the seal receiving portion 30b of seal receiving ring 30 and the small-diameter end portion of handle portion 33. A slit 34a is formed in a central portion of the seal member 34. The slit 34a has a substantially straight shape. When the trocar system 1 of this embodiment is used, the guide member 9 is inserted and assembled in the insertion portion 21 of dilator 8, as shown in FIG. 3. In this case, the distal end portion of the straight portion 28 of guide member 9 is held in the state in which it is projected from the breakage-prevention portion 25 of dilator 8 by a predetermined length. In this state, the handle section 29 of guide member 9 is held by the fingers, and the operation of axially pulling the handle section 29 of guide member 9 relative to the dilator 8 and the operation of pushing it are properly combined. Thereby, the amount of projection of the distal end portion of guide member 9, which projects from the distal end of the dilator 8, can be adjusted as desired.

The operation of the above-described structure will now be described. When the trocar system 1 of this embodiment is to be used, the handpiece unit 2 of the ultrasonic trocar is, in advance, set in the assembled state, as shown in FIG. 1, in which the trocar needle 6, tube 7, dilator 8 and guide member 9 are combined. At this time, the distal end portion of the straight portion 28 of guide member 9 is projected from the breakage-prevention portion 25 of dilator 8 by a predetermined length, and is kept in this state. In addition, the pierce needle 16 of trocar needle 6 is projected from the distal end of the straight portion 28 of guide member 9 and kept in this state.

The handpiece unit 2, in its assembled state as shown in FIG. 1, is operated so that the trocar tube 7 may pierce and penetrate the patient's skin and body wall and may stay therein. At the time of the piercing operation of the handpiece unit 2, the ultrasonic oscillation device 4 is activated by the operation of the output control device 5. At this time, energy for ultrasonic oscillation is supplied from the ultrasonic oscillation device 4 to the ultrasonic oscillation element 13 of handpiece unit 2 over the connection cable 3. Thus, the ultrasonic oscillation element 13 produces ultrasonic oscillation. The ultrasonic oscillation produced from the ultrasonic oscillation element 13 is amplified by the horn 14 and transmitted to the ultrasonic oscillation transmission rod 15. Thus, the mechanical oscillation of the ultrasonic oscillation element 13 is transmitted to the pierce needle 16 of trocar needle 6 at the distal end of the ultrasonic oscillation transmission rod 15 through the horn 14.

Figure 5C:
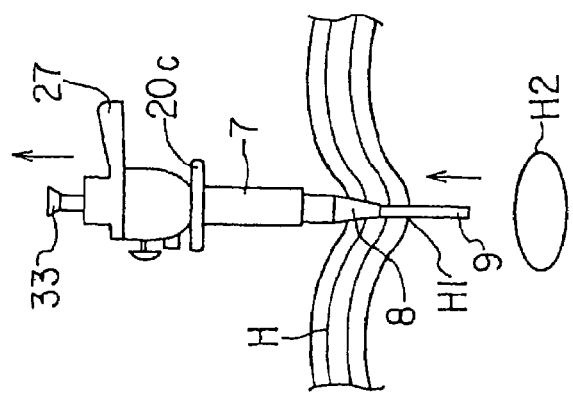
FIG. 5C is a side view showing a state in which the trocar needle has been drawn out of the assembly unit of the trocar apparatus.
Figure 5B:
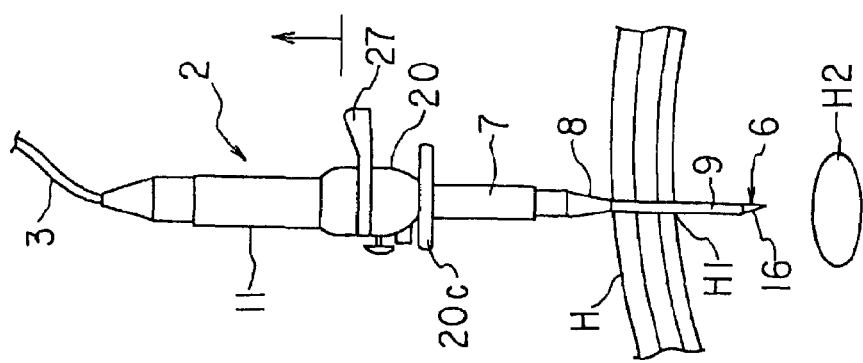
FIG. 5B is a side view showing a state in which the handpiece unit of the ultrasonic trocar has pierced the abdominal wall portion.
Figure 5A:
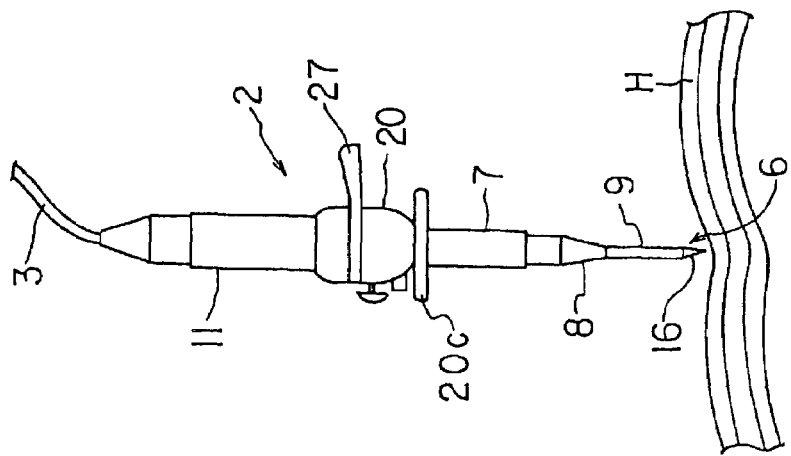
FIG. 5A is a side view showing a state before the handpiece unit of the ultrasonic trocar according to the first embodiment is made to pierce the abdominal wall portion.

Then, with the handpiece unit 2 being held, the pierce needle 16 of trocar needle 6 is made to pierce the patient's abdominal wall H, as shown in FIG. 5A. At this time, the pierce needle 16 of trocar needle 6 pierces the abdominal wall H in the state in which ultrasonic oscillation is being transmitted to the pierce needle 16 of trocar needle 6. Thus, the pierce needle 16 of trocar needle 6 is made to easily pierce the abdominal wall H with a weak force. With this operation, as shown in FIG. 5B, a small-diameter pierce hole H1 is made in the abdominal wall H.

As is shown in FIG. 5B, after the handpiece unit 2 has been inserted up to the location of the breakage-prevention portion 25 near the pierce hole expansion portion 24 of dilator 8, the trocar needle 6 alone is drawn out of the handpiece unit 2. In this state, the handpiece unit 2 is further inserted in the abdominal wall H. Thereby, as shown in FIG. 5C, the diameter of the small-diameter pierce hole H1 made by the trocar needle 6 is increased up to the outside diameter of the tube 7 by means of the conical portion of the pierce hole expansion portion 24 of dilator 8.

Prior to the work for increasing the diameter of the pierce hole H1, the following operation is performed when the distal end of the guide member 9, which is projected from the distal end of the dilator 8, is in the propinquity of an organ H2 in the abdominal cavity. Specifically, the handle section 29 of guide member 9 is held by the fingers and the handle section 29 of guide member 9 is axially pulled from the dilator 8. Thereby, the amount of projection of the distal end portion of the guide member 9, which projects from the distal end of the dilator 8, is decreased. At this time, the guide member 9 functions as a guide for the insertion of the dilator 8. In general terms, the body wall comprises a plurality of layers. Even if the pierce needle 16 has pierced the body wall, once the pierce needle 16 is pulled out of the body wall, the pierce holes in the respective layers of the body wall are displaced due to muscles. In particular, the peritoneum that is the deepest layer of the body wall may easily be displaced. If the guide member 9 is stayed in the body wall, the axis of insertion of the dilator 8 is guided by the guide member 9 while the pierce hole is being increased. This facilitates the work for increasing the diameter of the pierce hole.

In addition, while the diameter of the pierce hole H1 is being increased, the amount of projection of the distal end portion of guide member 9, which projects from the distal end of dilator 8, is adjusted in accordance with the distance between the organ H2 in the abdominal cavity and the distal end of straight portion 28 of guide member 9. In this work of adjusting the projection amount of guide member 9, the operation of axially pulling the handle section 29 of guide member 9 relative to the dilator 8 and the operation of axially pushing out the handle section 29 are properly combined. Thereby, the amount of projection of the distal end portion of guide member 9, which projects from the distal end of dilator 8, can be adjusted as desired.

Figure 6A:
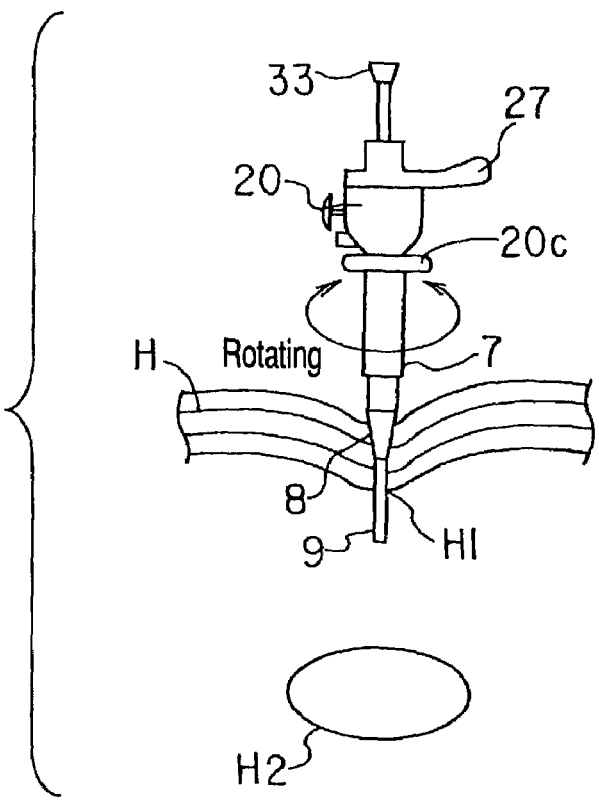
FIG. 6A is a side view illustrating the work for expanding the small-diameter pierce hole made by the trocar needle by means of the dilator.

When the diameter of the pierce hole H1 is to be increased, the operation of pushing the handpiece unit 2 into the abdominal wall H and the operation of rotating it about the center axis of the trocar tube 7, as indicated by an arrow in FIG. 6A, are simultaneously performed while the operation handle 27 of dilator 8 and the finger hook portion 20c of trocar tube 7 are being held. Thereby, with the operation of pushing the conical portion of the pierce hole expansion portion 24, the work for increasing the diameter of the small-diameter pierce hole H1 up to the outside diameter of tube 7 is performed. At the time of this work, the insertion portion 19 of trocar tube 7 is successively inserted into the pierce hole H1 that has been enlarged by the pierce hole expansion portion 24 of dilator 8 up to a diameter substantially equal to the diameter of the insertion portion 19 of trocar tube 7. Thus, the insertion portion 19 of trocar tube 7 is inserted in the pierce hole H1.

Figure 6B:
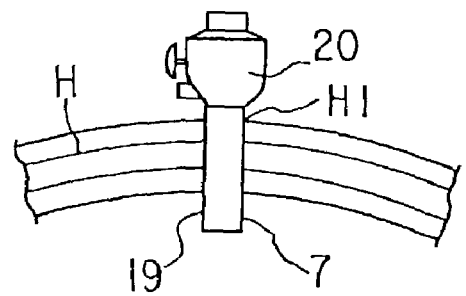
FIG. 6B is a side view showing a state in which the assembly unit comprising the dilator and guide member has been drawn out of the trocar tube.

Once the insertion portion 19 of trocar tube 7 has been inserted in the pierce hole H1, the insertion portion 19 of trocar tube 7 is relatively firmly fixed in the pierce hole H1 in the abdominal wall H by the elasticity of the peripheral tissue of the pierce hole H1 enlarged by the insertion of the insertion portion 19. In this state, as shown in FIG. 6B, the assembly unit of the dilator 8 and guide member 9 is drawn out of the trocar tube 7. Thus, the trocar tube 7 is inserted and stayed in the pierce hole H1 of abdominal wall H.

With the above structure, the following advantages can be obtained. The trocar system 1 of this embodiment includes the soft cylindrical guide member 9 projected from the distal end of the dilator 8 that is interposed between the tube 7 and trocar needle 6. Thus, when the small-diameter pierce hole H1 made by the trocar needle 6 is to be enlarged up to the outside diameter of the tube 7 by the conical portion of the pierce hole expansion portion 24 of dilator 8, the guide member 9 can be put in contact with the organ H2 in the abdominal cavity before the distal end portion of the dilator 8 comes in contact with the organ H2 in the abdominal cavity. Accordingly, during the dilation operation, the distal end portion of dilator 8 is surely prevented from coming in contact with the organ H2 in the abdominal cavity, and the safety in the dilation operation is enhanced.

While the handle section 29 of guide member 9 is being held by the fingers, the operation of axially pulling the handle section 29 of guide member 9 relative to the dilator 8 and the operation of pushing it out are properly combined. Thereby, the amount of projection of the distal end portion of guide member 9, which projects from the distal end of the dilator 8, can be desirably adjusted. Accordingly, the amount of projection of the distal end portion of guide member 9 can be desirably adjusted in accordance with conditions such as the thickness of the abdominal wall H that is to be pierced by the trocar tube 7, or the distance from the organ H2. As a result, the organ H2 in the abdominal cavity will never be pressed during the dilation operation for increasing the diameter of the small-diameter pierce hole H1 made in the abdominal wall H by the trocar needle 6 up to the outside diameter of tube 7. Moreover, the work for inserting and staying the tube 7 in the abdominal wall H can be carried out easily and quickly.

The straight breakage-prevention portion 25 is provided at the distal conical end portion of the pierce hole expansion portion 24 of dilator 8. Thus, when a lateral force acts on the soft guide member 9 projecting from the distal end of dilator 8, the force acting in such a direction as to bend the guide member 9 at the distal conical portion of the pierce hole expansion hole 24 of dilator 8 can be dispersed over the wide area of the straight breakage-prevention section 25 of dilator 8. Accordingly, the conical distal portion of the pierce hole expansion portion 24 of dilator 8 is prevented from exerting a large local bending force to the guide member 9, and the guide member 9 is protected against bending.

During the dilation operation, the breakage-prevention portion 25 of dilator 8 can be made to function also as the guide member for the dilation work. Thus, the operability of the dilation work of dilator 8 can be enhanced.

In the present embodiment, the second O-ring 32 is fitted on the outer periphery of the alignment portion 28a of guide member 9. Further, the three O-ring engagement grooves 21a, 21b and 21c are formed in the inner periphery of the insertion portion 21 of dilator 8 in the direction of insertion of the guide member 9. When the guide member 9 is pulled from the insertion portion 21 of dilator 8, the second O-ring 32 of guide member 9 is detachably engaged with the O-ring engagement grooves 21a, 21b and 21c in succession. Accordingly, when the guide member 9 is drawn out of the insertion portion 21 of dilator 8, the user can sense a click and recognize the amount of draw-out of the guide member 9 by sensing. As a result, the amount of projection of the distal end portion of guide member 9, which cannot directly be observed by the naked eye, can easily be recognized.

Figure 7:
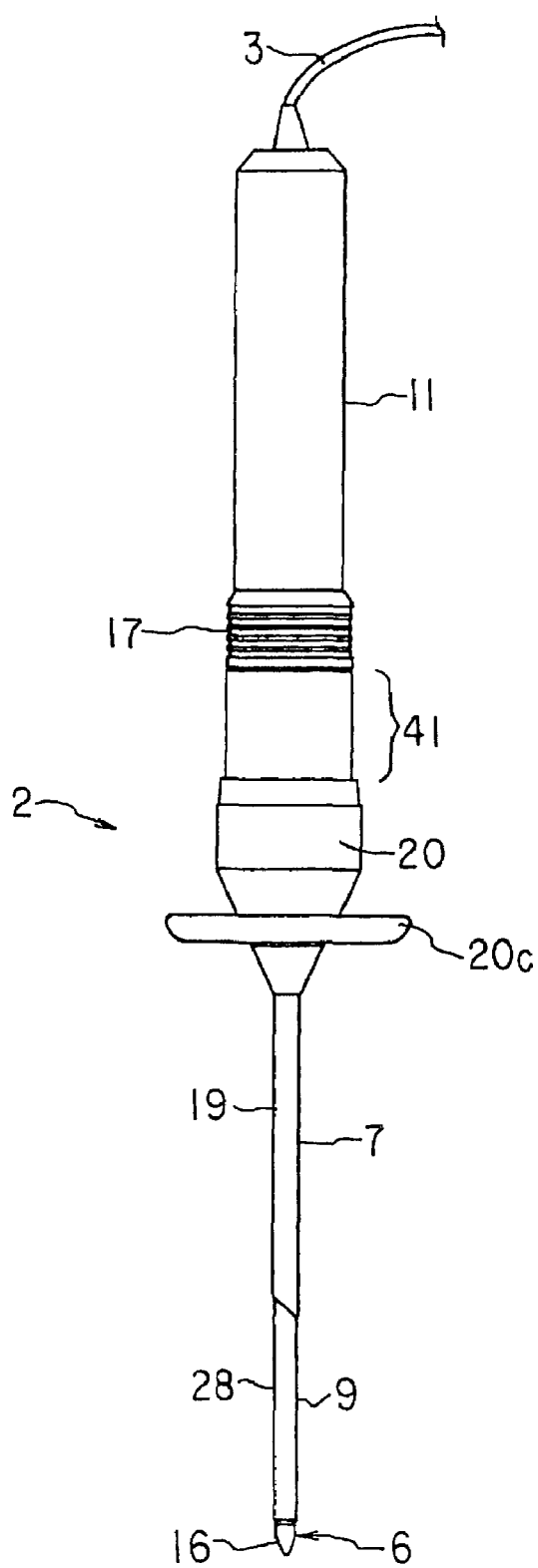
FIG. 7 is a side view showing a handpiece unit, in its assembled state, of an ultrasonic trocar in a trocar system according to a second embodiment of the invention.
Figure 8:
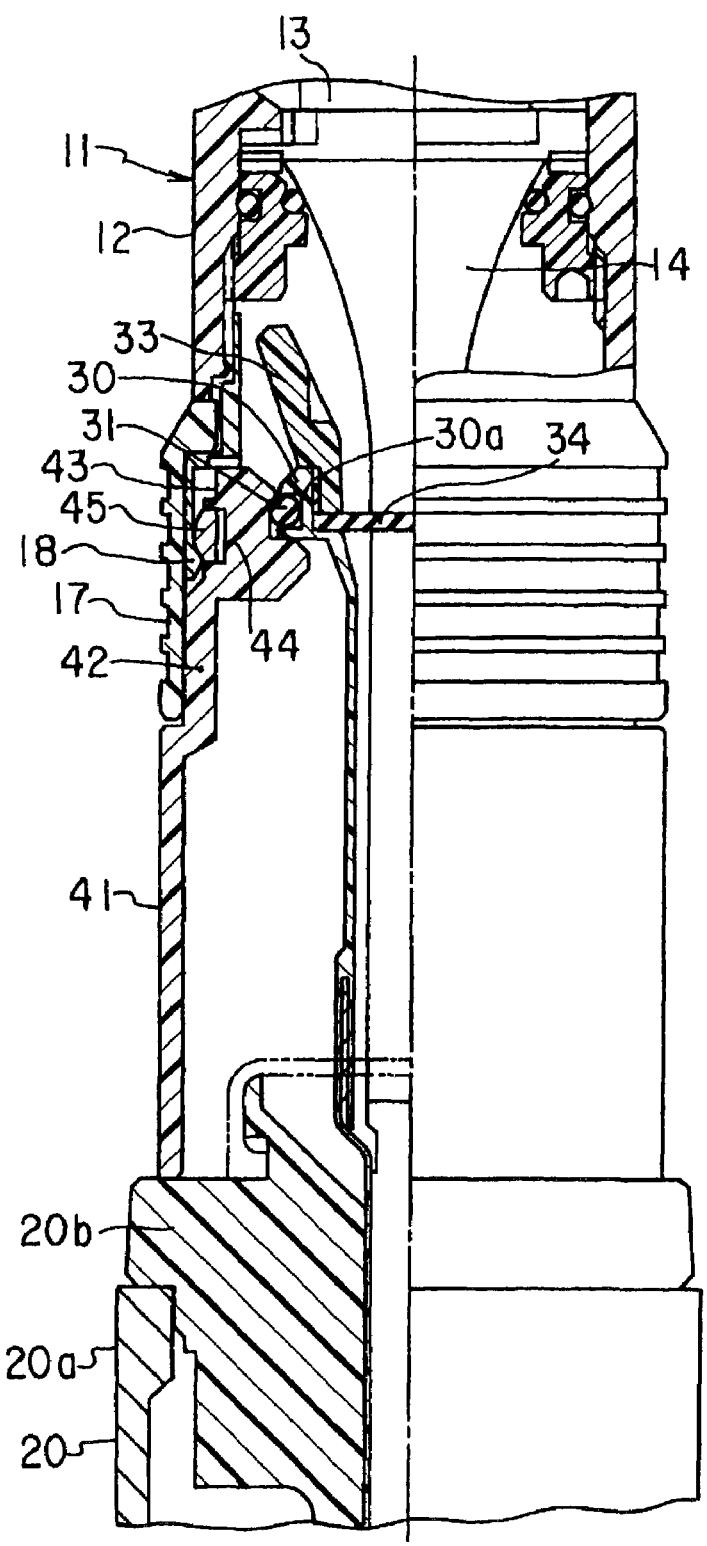
FIG. 8 is a partial cross-sectional side view showing an internal structure of the main part of the handpiece unit of the second embodiment.

FIGS. 7 and 8 show a second embodiment of the present invention. This embodiment is made by altering the structure of the handpiece unit 2 of the trocar system of the first embodiment (see FIGS. 1 to 6B) in the following fashion. Except for the altered portions, the handpiece unit 2 has the same structure as that in the first embodiment and a description thereof is omitted.

Specifically, in this embodiment, the tube 7 has the insertion portion 19 having a relatively small diameter (e.g. about 5 mm) and a short length. The inside diameter of the insertion portion 19 of tube 7 is set to be substantially equal to, for example, the outside diameter of the straight portion 28 of guide member 9. In this embodiment, the dilator 8 of the first embodiment is omitted. As shown in FIG. 7, the straight portion 28 of the guide member 9 is directly inserted in the insertion portion 19 of tube 7.

Furthermore, in this embodiment, a cylindrical spacer 41 for wavelength adjustment of ultrasonic oscillation is provided between the proximal end portion 20 of tube 7 and the handle 11 of trocar needle 6. As is shown in FIG. 8, a small-diameter trocar needle coupling portion 42 is provided at one of the spacer 41. The connection member 17 of trocar needle 6 is detachably fitted on the coupling portion 42.

A small-diameter cylindrical portion 43 is provided at the distal end of the coupling portion 42 of spacer 41. An annular C-ring receiving groove 44 is formed in the outer periphery of the small-diameter cylindrical portion 43. A C-ring 45 for engaging the trocar needle 6 is fitted in the receiving groove 44. The C-ring 45 is disposed at a position corresponding to the C-ring receiving portion 18 of connection member 17 of trocar needle 6. When the trocar needle 6 and spacer 41 are to be coupled, the connection member 17 of trocar needle 6 is fitted on the coupling portion 42 of spacer 41. In this state, the C-ring 45 of trocar needle coupling portion 42 is detachably engaged in the C-ring receiving portion 18 of trocar needle 6 to prevent disengagement.

When the guide member 9 is inserted in the tube 7 for assembly, the first C-ring 31 of guide member 9 is pressed on the inner periphery of the small-diameter cylindrical portion 43 of spacer 41. Thus, seal is effected between the seal receiving ring 30 and the small-diameter cylindrical portion 43 of spacer 41.

The embodiment with the above-described structure has the following advantages. In this embodiment, the cylindrical spacer 41 for wavelength adjustment of ultrasonic oscillation is provided between the proximal end portion 20 of tube 7 and the handle 11 of trocar needle 6. Thereby, the length of the spacer 41 can be adjusted in accordance with the oscillation characteristics of the ultrasonic oscillation produced by the ultrasonic oscillation element 13 and transmitted to the probe 10 of trocar needle 6. Even in the case of using a model wherein the diameter of the insertion portion 19 of tube 7 is relatively small and the length thereof is small, the length of the spacer 41 may be adjusted. Thus, like the first embodiment wherein the dilator 8 is interposed between the tube 7 and trocar needle 6, the handpiece unit 2 of the ultrasonic trocar can perform ultrasonic treatment.

Figure 9A:
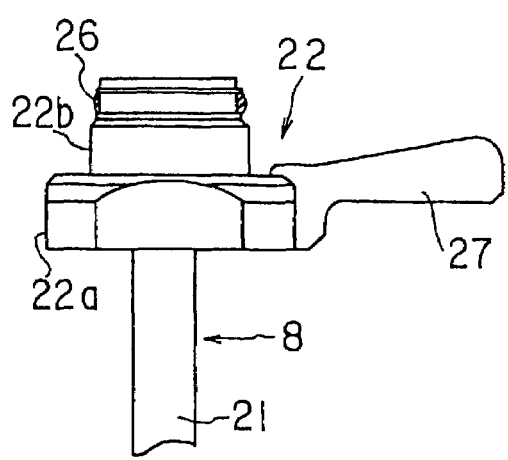
FIG. 9A is a side view showing a handle portion of a dilator of a handpiece unit of an ultrasonic trocar in a trocar system according to a third embodiment of the invention.
Figure 9B:
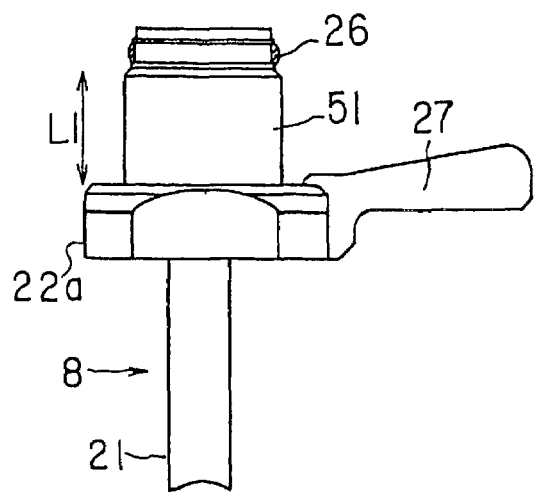
FIG. 9B is a side view showing an upper part of the handle portion of the dilator.

FIGS. 9A and 9B show a third embodiment of the present invention. This embodiment is made by altering the structure of the dilator 8 of handpiece unit 2 of the trocar system of the first embodiment (see FIGS. 1 to 6B) in the following fashion. Except for the altered portions, the handpiece unit 2 has the same structure as that in the first embodiment and a description thereof is omitted.

Specifically, in this embodiment, a plurality of models wherein the small-diameter cylindrical portions 22b of proximal end portions 22 of dilators 8 have different lengths L1 are prepared in advance. For example, a model with a smaller axial length L1 of the small-diameter cylindrical portion 22b, as shown in FIG. 9A, and a model with a greater axial length L1 of a small-diameter cylindrical portion 51, as shown in FIG. 9B, are prepared in advance. In accordance with the length of the insertion portion 19 of trocar tube 7, the dilator 8 with a proper length L1 of the small-diameter cylindrical portion 22b, 51 is selectively used.

In this embodiment, in accordance with the variation in conditions, such as the length of the insertion portion 19 of trocar tube 7, the dilator 8 with a proper axial length L1 of the small-diameter cylindrical portion 22b, 51 is selectively used. Thereby, the position of the pierce hole expansion portion 24 of dilator 8 can properly be adjusted.

Figure 10A:
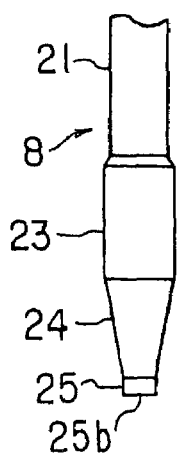
FIG. 10A is a side view showing a main part of a first modification of the dilator of the first embodiment.

FIG. 10A shows a first modification of the dilator 8 of the handpiece unit 2 according to the first embodiment (see FIGS. 1 to 6B). In this modification, the distal end portion of the breakage-prevention portion 25 of dilator 8 is provided with a flat face 25b formed in a direction perpendicular to the center axis of the insertion portion 21. In addition, in this modification, the length of the breakage-prevention portion 25 of dilator 8 is set to be less than the length S of the breakage-prevention portion 25 of dilator 8 in the first embodiment. The dilator 8 of this modification can be used similarly with the first embodiment.

Figure 10B:
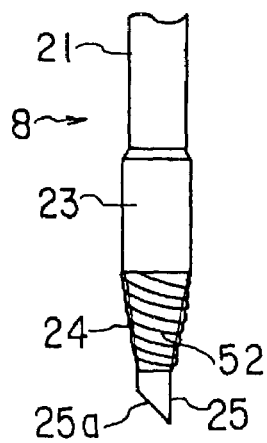
FIG. 10B is a side view showing a main part of a second modification of the dilator of the first embodiment.

FIG. 10B shows a second modification of the dilator 8 of the handpiece unit 2 according to the first embodiment (see FIGS. 1 to 6B). In this modification, the tapered surface of the pierce hole expansion portion 24 has threaded grooves 52. In this case, when the pierce hole H1 is dilated by the pierce hole expansion portion 24 of dilator 8, the pierce hole expansion portion 24 of dilator 8 is rotated. Thereby, the operation for enlarging the pierce hole H1 can be promoted by the threaded grooves 52 in the tapered surface of the pierce hole expansion portion 24.

Figure 10C:
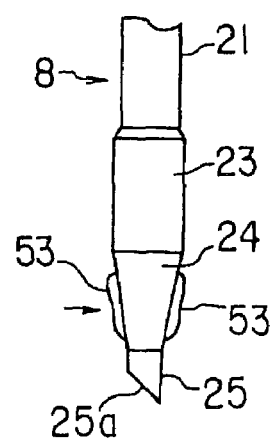
FIG. 10C is a side view showing a main part of a third modification of the dilator of the first embodiment.
Figure 10D:
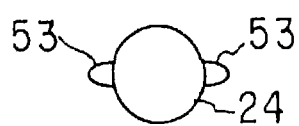
FIG. 10D is a cross-sectional view taken along line 10D—10D in FIG. 10C.

FIGS. 10C and 10D show a third modification of the dilator 8 of the handpiece unit 2 according to the first embodiment (see FIGS. 1 to 6B). In this modification, the tapered surface of the pierce hole expansion portion 24 is provided with two projections 53. The two projections 53 extend in the axial direction on the tapered surface of the pierce hole expansion portion 24. In this case, when the pierce hole H1 is to be enlarged by the pierce hole expansion portion 24 of dilator 8, the pierce hole expansion portion 24 of dilator 8 can be axially pushed out while the rotation of the dilator 8 is prevented by the two projections 53. Therefore, in this modification, compared to the case of rotating the dilator 8, the pierce hole H1 can be more easily enlarged. In addition, twisting of the peripheral part of the pierce hole H1 due to rotation of dilator 8 can be prevented.

Figure 11A:
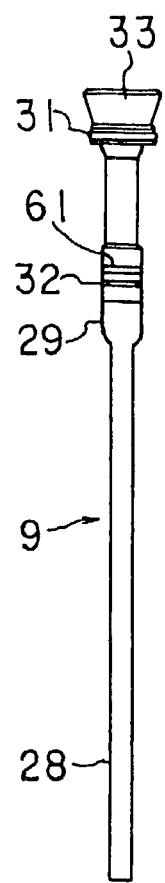
FIG. 11A is a side view showing a main part of a first modification of the guide member of the first embodiment.

FIG. 11A shows a first modification of the guide member 9 of the handpiece unit 2 according to the first embodiment (see FIGS. 1 to 6B). In this modification, the handle section 29 of guide member 9 is provided with a colored line 61. When the guide member 9 is drawn out of the dilator 8, the line 61 on the handle portion 29 of guide member 9 is viewed by the eye and the amount of projection of the guide member 9 is indicated.

Figure 11B:
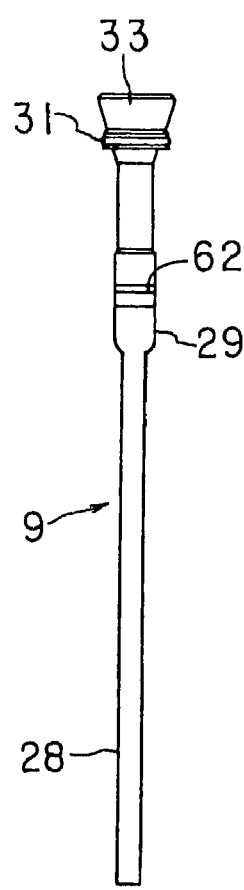
FIG. 11B is a side view showing a main part of a second modification of the guide member of the first embodiment.

FIG. 11B shows a second modification of the guide member 9 of the handpiece unit 2 according to the first embodiment (see FIGS. 1 to 6B). In this modification, the handle section 29 of guide member 9 is provided with a click mechanism 62. When the guide member 9 is drawn out of the dilator 8, the amount of draw-out of the guide member 9 is indicated by the sensing obtained by the operation of the click mechanism 62.

Figure 11C:
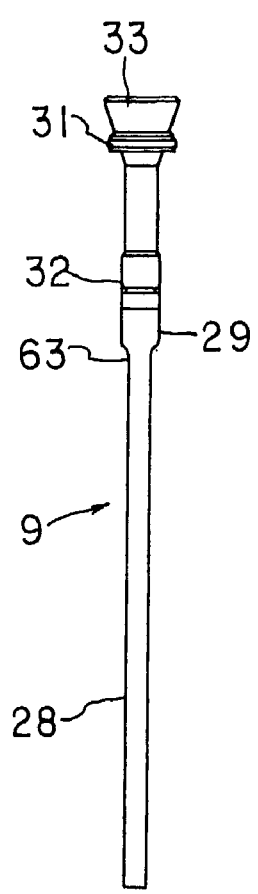
FIG. 11C is a side view showing a main part of a third modification of the guide member of the first embodiment.

FIG. 11C shows a third modification of the guide member 9 of the handpiece unit 2 according to the first embodiment (see FIGS. 1 to 6B). In this modification, the handle section 29 of guide member 9 is provided with a whistle-shaped portion 63 that produces an air leak sound. When the guide member 9 is drawn out of the dilator 8, an air leak sound produced through the whistle-shaped portion 63 of handle section 29 of guide member 9 is heard and the amount of draw-out of the guide member 9 is indicated.

FIG. 12A shows a fourth modification of the guide member 9 of the handpiece unit 2 according to the first embodiment (see FIGS. 1 to 6B). In this modification, the distal end portion of the straight portion 28 of guide member 9 is provided with a reformed bending portion 71 curved away from the center axis of the straight portion 28. In this modification, when the guide member 9 has been inserted in the abdominal cavity through the pierce hole H1 in the patient's abdominal wall H, the bending portion 71 at the distal end of the straight portion 28 of guide member 9 is curved away from the center axis of the straight portion 28. Thereby, contact with the organ H2 in the abdominal cavity can be avoided.

FIG. 12B shows a fifth modification of the guide member 9 of the handpiece unit 2 according to the first embodiment (see FIGS. 1 to 6B). In this modification, the distal end portion of the straight portion 28 of guide member 9 is provided with a bellows-shaped extensible portion 72. In this modification, when the guide member 9 has been inserted in the abdominal cavity through the pierce hole H1 in the patient's abdominal wall H and the distal end of the straight portion 28 of guide member 9 has come in contact with the organ H2 in the abdominal cavity, the extensible portion 72 easily contracts. Thereby, a large pressing force is prevented from acting on the organ H2 in the abdominal cavity.

FIG. 12C shows a sixth modification of the guide member 9 of the handpiece unit 2 according to the first embodiment (see FIGS. 1 to 6B). In this modification, the distal end portion of the straight portion 28 of guide member 9 is provided with an axially extending slit 73. In this modification, when the guide member 9 has been inserted in the abdominal cavity through the pierce hole H1 in the patient's abdominal wall H and the distal end of the straight portion 28 of guide member 9 has come in contact with the organ H2 in the abdominal cavity, the surrounding portion of the slit 73 of the straight portion 28 expands to both lateral sides and contracts by a proper length L3. Thereby, a large pressing force is prevented from acting on the organ H2 in the abdominal cavity.

FIG. 13A shows a seventh modification of the guide member 9 of the handpiece unit 2 according to the first embodiment (see FIGS. 1 to 6B). In this modification, the straight portion 28 of guide member 9 is formed of, e.g. PFA, to have a thin portion. Thus, a deformation-promotion section 74 which tends to easily bend is formed. In this modification, when the guide member 9 has been inserted in the abdominal cavity through the pierce hole H1 in the patient's abdominal wall H and the distal end of the straight portion 28 of guide member 9 has come in contact with the organ H2 in the abdominal cavity, the deformation-promotion section 74 easily bend. Thereby, a large pressing force is prevented from acting on the organ H2 in the abdominal cavity.

FIG. 13B shows an eighth modification of the guide member 9 of the handpiece unit 2 according to the first embodiment (see FIGS. 1 to 6B). In this modification, the distal end portion of the straight portion 28 of guide member 9 is provided with, e.g. many pores 75. Thus, a deformation-promotion section 74 which tends to easily bend is formed. In this modification, when the guide member 9 has been inserted in the abdominal cavity through the pierce hole H1 in the patient's abdominal wall H and the distal end of the straight portion 28 of guide member 9 has come in contact with the organ H2 in the abdominal cavity, the deformation-promotion section 74 easily bends. Thereby, a large pressing force is prevented from acting on the organ H2 in the abdominal cavity.

FIGS. 14A and 14B shows a fourth embodiment of the present invention. In this embodiment, the structure of the handpiece unit 2 of the trocar system of the first embodiment (see FIGS. 1 to 6B) is altered in the following fashion.

In this embodiment, as shown in FIG. 14A, a head 81 of the proximal end portion 22 of dilator 8 is provided with an axially extending guide groove 82. An operation wire 83 for pulling up the guide member 9 is passed through the guide groove 82. A ring 84 for hooking of the finger or the like is coupled to an outer end portion of the operation wire 83.

As is shown in FIG. 14B, a plurality of band-like index rings 91 indicative of length are axially juxtaposed on the outer periphery of the straight portion 28 of guide member 9. For example, when an endoscopic image of the abdominal cavity is observed, the index rings 91 provided on the distal projecting portion of the guide member 9, which projects from the breakage-prevention portion 25 of dilator 8, is viewed by the eye. Thereby, the amount of projection of the distal end portion of the guide member 9, which projects from the breakage-prevention portion 25 of dilator 8, is recognized.

The embodiment with the above structure has the following advantages. Specifically, this embodiment includes the operation wire 83 for pulling up the guide member 9. With the finger or the like hooked in the ring 84 provided at the outer end of the operation wire 83, the operation wire 83 is pulled. Thereby, the guide member 9 can be pulled up. Therefore, the amount of projection of the distal end portion of the guide member 9, which projects from the distal end of dilator 8, can desirably be adjusted. In this embodiment, like the first embodiment, the amount of projection of the distal end portion of the guide member 9 can desirably be adjusted in accordance with conditions such as the thickness of the abdominal wall H that is to be pierced by the trocar tube 7, or the distance from the organ H2. As a result, the organ H2, etc., in the abdominal cavity will never be pressed during the dilation operation for increasing the diameter of the small-diameter pierce hole H1 made in the abdominal wall H by the trocar needle 6 up to the outside diameter of tube 7. Moreover, the work for inserting and staying the tube 7 in the abdominal wall H can be carried out easily and quickly.

In the fourth embodiment (see FIGS. 14A and 14B), the index rings 91 on the distal end portion of guide member 9 may be replaced with numeral indices 92 indicative of length, as shown in FIG. 14C.

FIG. 15 shows a fifth embodiment of the invention. In this embodiment, the structure of the guide member 9 of handpiece unit 2 of the first embodiment (see FIGS. 1 to 6B) is altered in the following fashion.

In this embodiment, a distal end portion of the straight portion 28 of guide member 9 is provided with a bending portion 102 comprising a plurality of bending elements 101. In this bending portion 102, the bending elements 101 are rotatably juxtaposed in the axial direction of the straight portion 28 of guide member 9.

Two operation wires 104 for bending the bending portion 102 are passed through the guide member 9. A distal end portion of each operation wire 104 is fixed at the foremost bending element 101 of the bending portion 102.

Two wire insertion holes 103 are formed in a proximal portion of the handle section 29 of guide member 9. A proximal end portion of each operation wire 104 is extended from the associated wire insertion hole 103 to the outside of guide member 9. An outer end portion of each operation wire 104 is connected to a ring 105 for hooking of the finger or the like.

In this embodiment, with the finger or the like hooked in the ring 105 provided at the outer end of the operation wire 104, the operation wire 104 is pulled. Thereby, the bending of the bending portion 102 is controlled. Therefore, when the guide member 9 has been inserted in the abdominal cavity through the pierce hole H1 in the patient's abdominal wall H, the bending portion 102 at the distal end of the straight portion 28 of guide member 9 is operated so as to avoid contact with the organ H2 in the abdominal cavity.

Figure 16:
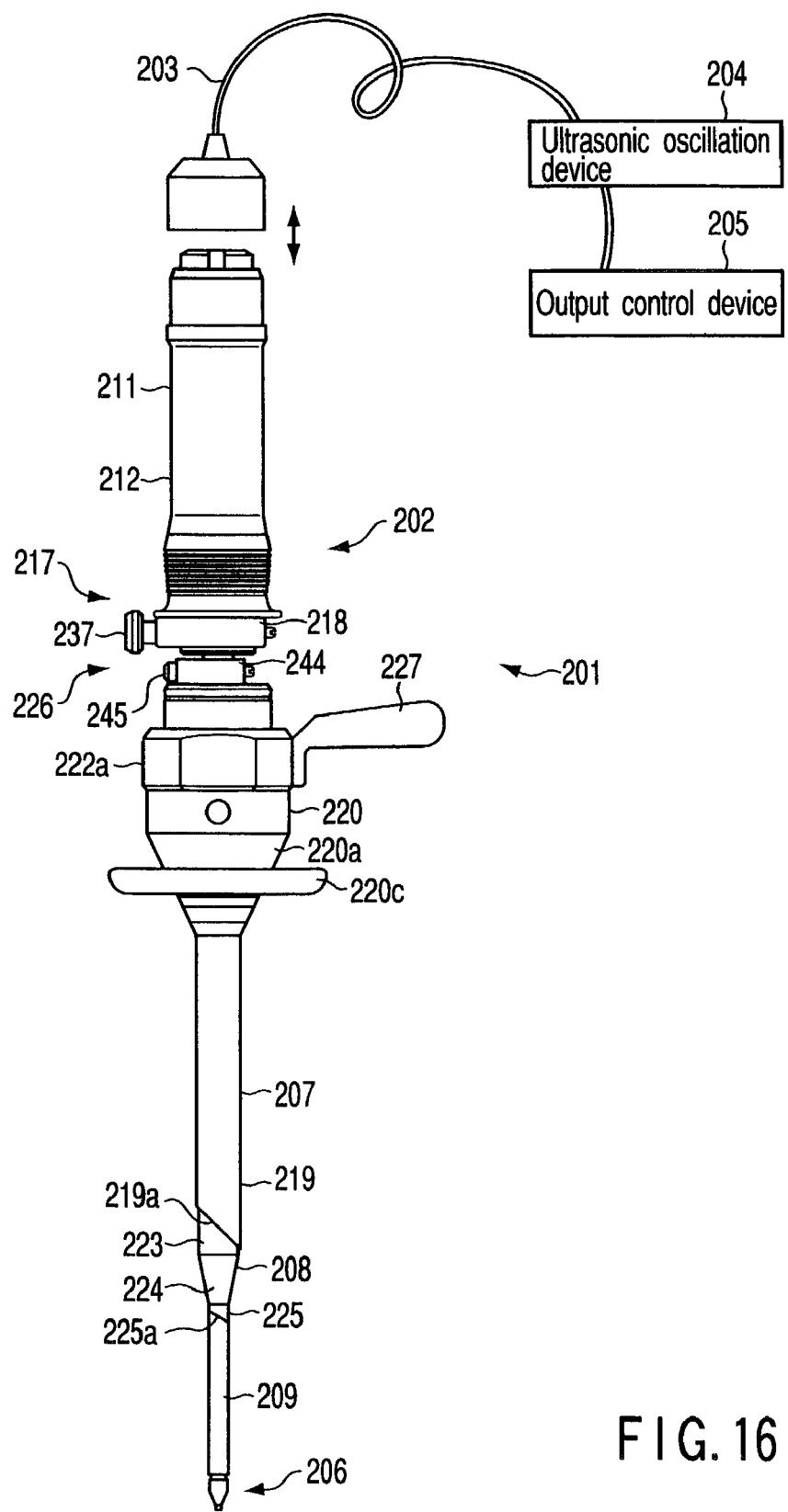
FIG. 16 is a side view showing a handpiece unit, in its assembled state, of an ultrasonic trocar in a trocar system according to a sixth embodiment of the invention.

FIGS. 16 to 25 show a sixth embodiment of the invention. FIG. 16 schematically shows the entire structure of a trocar system 201 according to this embodiment. This trocar system 201 is provided with a handpiece unit 202 of an ultrasonic trocar, which is held and operated by the operator. The handpiece unit 202 is connected to an ultrasonic oscillation device 204 over a connection cable 203. The ultrasonic oscillation device 204 supplies energy for ultrasonic oscillation. The ultrasonic oscillation device 204 is connected to an output control device 205, such as a foot switch or a hand switch, for controlling energy output.

The handpiece unit 202 of the ultrasonic trocar comprises a trocar needle 206 for piercing into the body wall; a tube 207 in which the trocar needle 206 is inserted; a dilator 208 inserted between the tube 207 and trocar needle 206; and a guide member 209 formed of a soft cylindrical member and inserted in the dilator 208. The guide member 209 may be formed of a hard member. The handpiece unit 202 of the ultrasonic trocar of this embodiment is selectively used in two modes: an assembled mode in which the trocar needle 206, tube 207, dilator 208 and guide member 209 are combined, and a disassembled mode in which these elements are separated. FIG. 16 shows a state in which the trocar needle 206, tube 207, dilator 208 and guide member 209 are combined.

Figure 17:
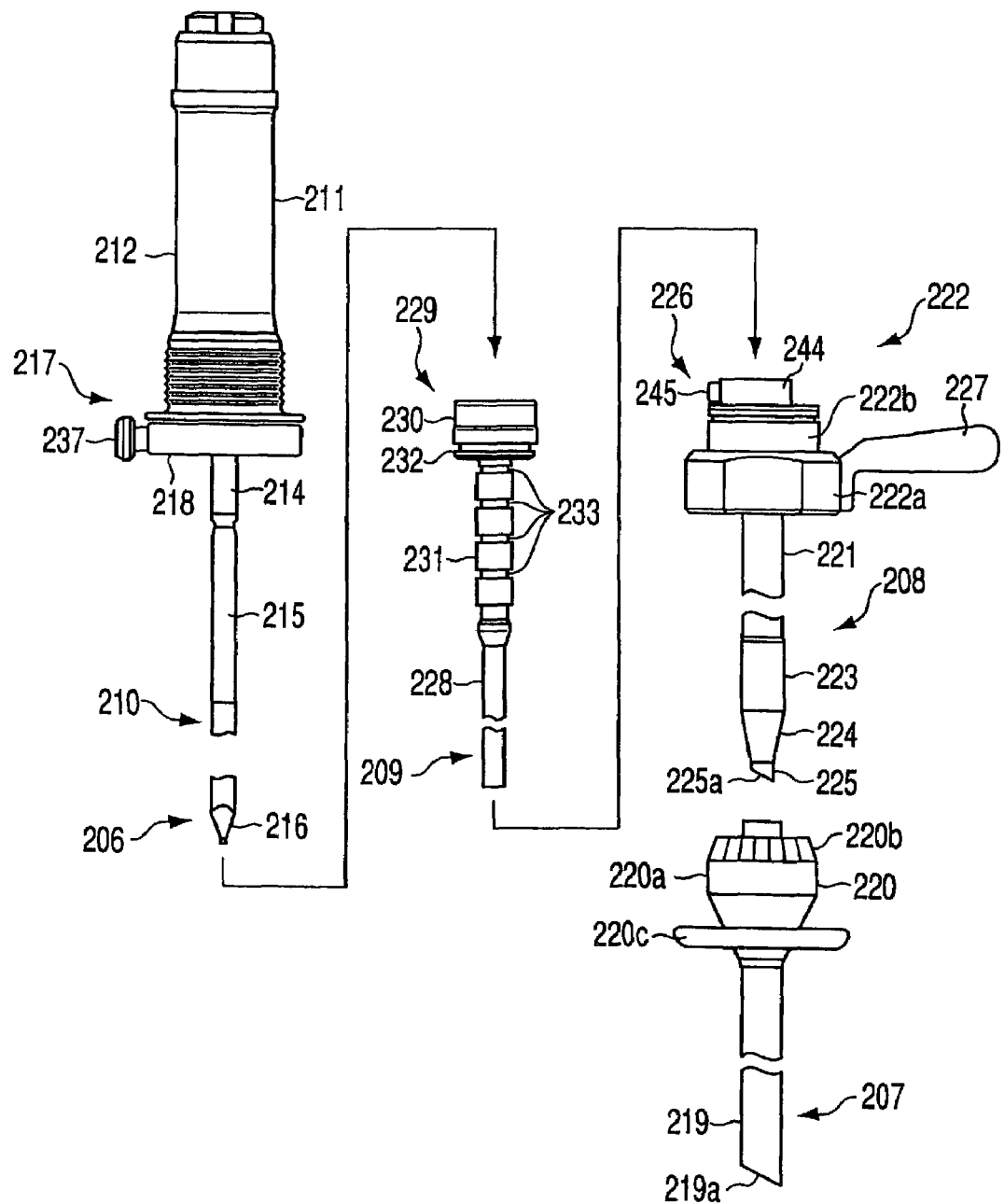
FIG. 17 is a side view showing the ultrasonic trocar of the sixth embodiment in its disassembled state.
Figure 18:
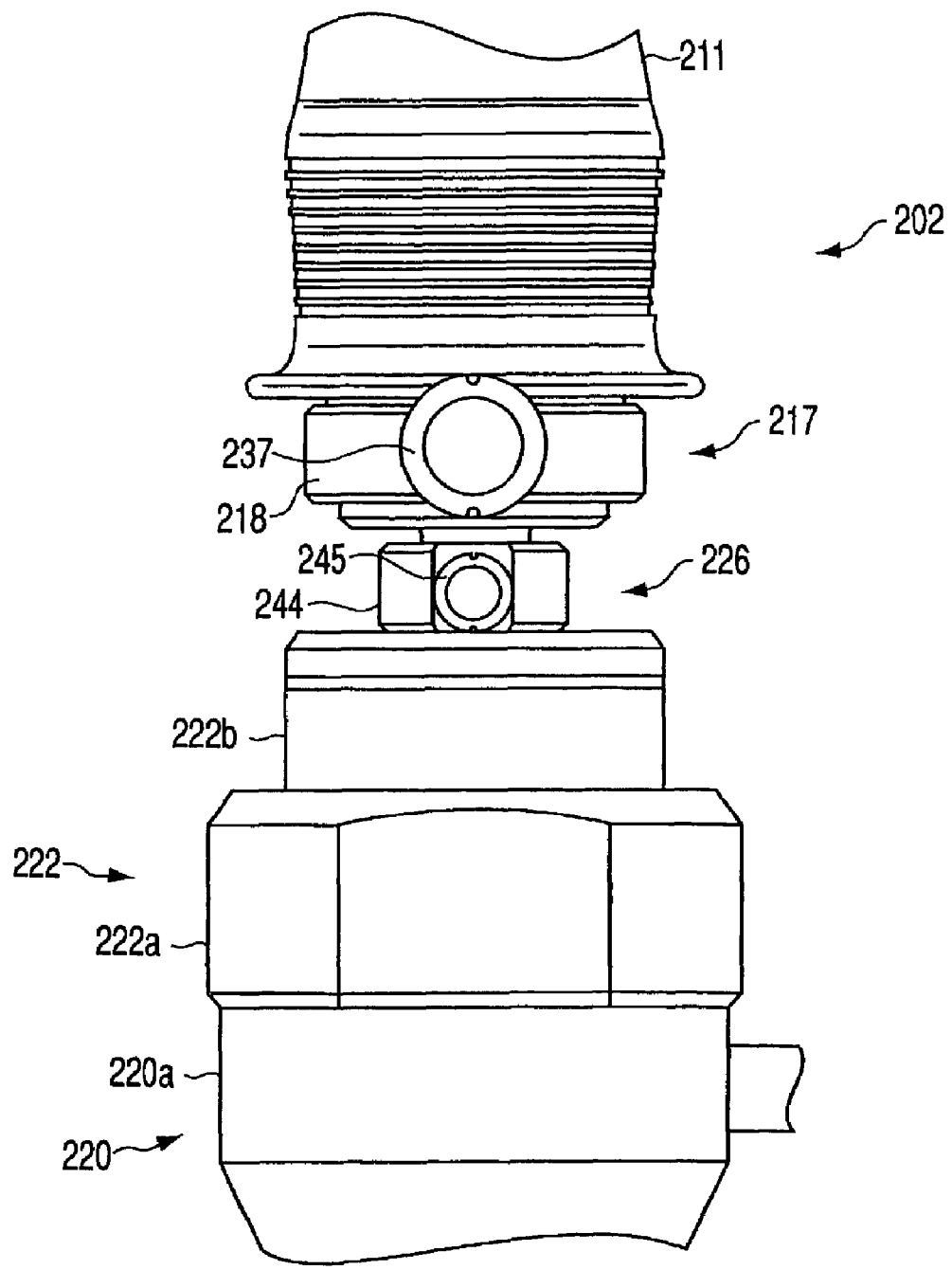
FIG. 18 is a side view showing a main part of the ultrasonic trocar of the sixth embodiment in its assembled state.

The trocar needle 206 is provided with a substantially straight probe 210, as shown in FIG. 17. A proximal-side handle 211 is disposed at a proximal end portion of the probe 210. The proximal-side handle 211 is provided with a substantially cylindrical housing 212.

Figure 19:
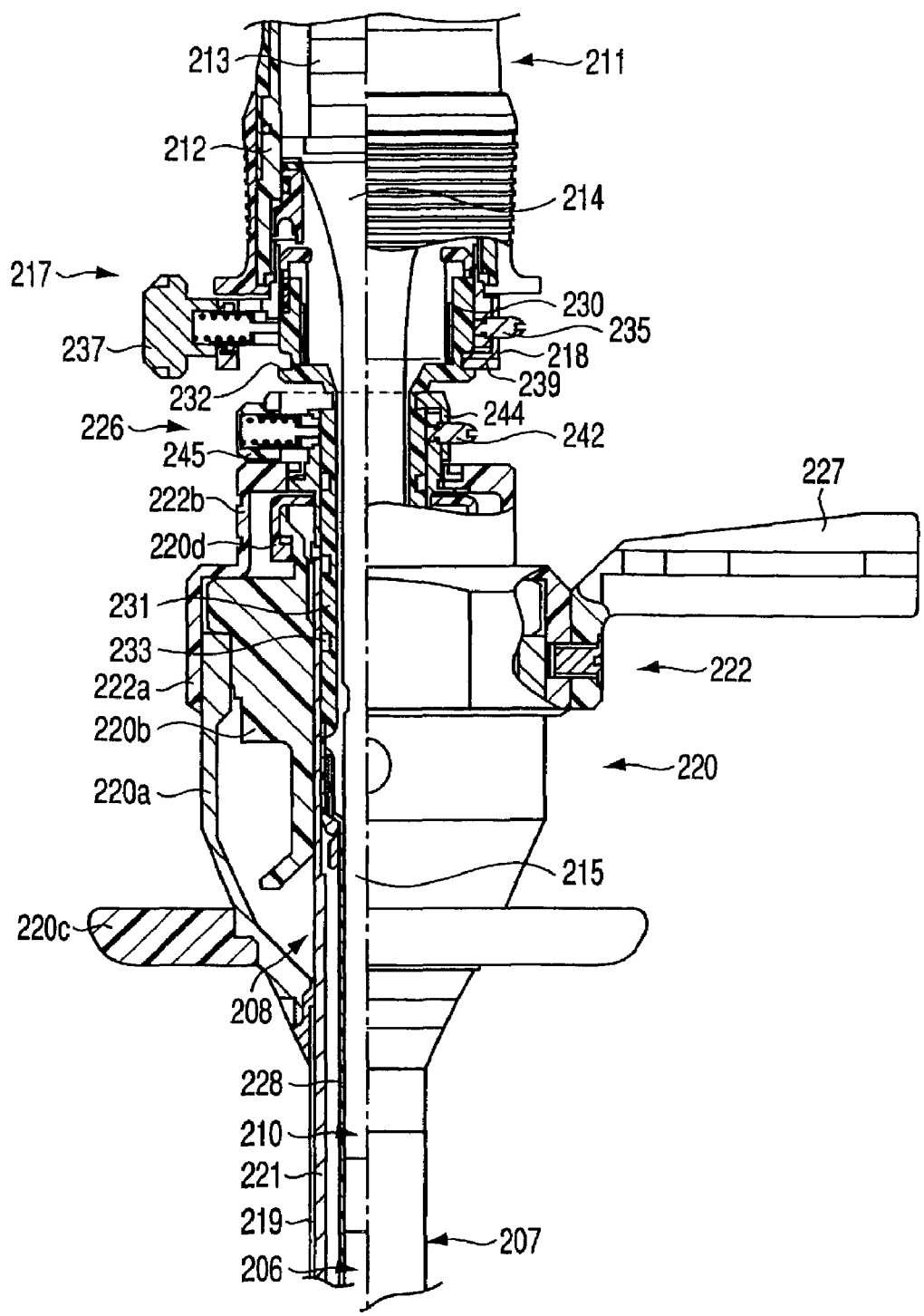
FIG. 19 is a vertical cross-sectional view showing a main part of the ultrasonic trocar of the sixth embodiment in its assembled state.

As is shown in FIG. 19, the housing 212 includes an ultrasonic oscillation element 213 that is an element for producing ultrasonic oscillation. A horn 214 for amplifying ultrasonic oscillation is disposed at a distal end portion of the ultrasonic oscillation element 213. A distal end portion of the horn 214 extends forward from the end of the housing 212. The distal end portion of the horn 214 is detachably screwed to a proximal end portion of an ultrasonic oscillation transmission rod (oscillation transmission rod) 215. A distal end of the oscillation transmission rod 215 is provided with a tapered pierce needle (needle body) 216. The pierce needle 216 is tapered, for example, in a conical shape, a trigonal pyramidal shape or a quadrangular pyramidal shape. Thereby, mechanical oscillation of the ultrasonic oscillation element 213 is transmitted to the distal-end pierce needle 216 provided at the distal end of the ultrasonic oscillation transmission rod 215. A guide member lock mechanism 217 (to be described later) is provided at a lower end portion of the handle 211. The guide member 209 is releasably locked by the guide member lock mechanism 217.

As is shown in FIG. 17, the trocar tube 207 has a tubular insertion portion 219 with a relatively large diameter (e.g. about 13 mm). A proximal end portion 220 is provided at a proximal end of the insertion portion 219. A distal end portion of the insertion portion 219 has a distal bevel face 219a. The distal bevel face 219a is inclined to a direction perpendicular to the center axis of the insertion portion 219. The proximal end portion 220 has a large-diameter cylindrical portion 220a. An insertion guide member 220b is engaged with an opening end portion of the large-diameter cylindrical portion 220a. A substantially flange-shaped finger hook portion 220c is formed on the outer periphery of the large-diameter cylindrical portion 220a.

As is shown in FIG. 19, the insertion guide member 220b is provided with a seal member 220d such as a valve (not shown), which effects sealing within the tube when an insertion instrument is inserted in the tube 207.

As is shown in FIG. 20B, the dilator 208 has a tubular insertion portion 221. A proximal end portion 222 is provided at a proximal end of the insertion portion 221. A large-diameter distal straight portion 223 for alignment is provided at a distal end of the insertion portion 221. The outside diameter of the distal straight portion 223 is set to be substantially equal to the inside diameter of the insertion portion 219 of tube 207. A distal end portion of the distal straight portion 223 is provided with a pierce hole expansion portion 224 having a substantially conical tapered shape.

A conical distal end portion of the pierce hole expansion portion 224 is provided with a straight breakage-prevention portion 225. The length of the breakage-prevention portion 225 is set at a predetermined value, as measured from the conical distal end of the pierce hole expansion portion 224. A distal end portion of the breakage-prevention portion 225 is provided with a distal bevel face 225a. The distal bevel face 225a is inclined to a direction perpendicular to the center axis of the insertion portion 221.

The proximal end portion 222 of dilator 208 includes a large-diameter cylindrical portion 222a. Over the large-diameter cylindrical portion 222a, there is provided a small-diameter cylindrical portion 222b having a smaller diameter than the cylindrical portion 222a. As is shown in FIG. 19, the inside diameter of the large-diameter cylindrical portion 222a is set to be substantially equal to the outside diameter of the large-diameter cylindrical portion 220a of trocar tube 207. When the dilator 208 and trocar tube 207 are coupled, the large-diameter cylindrical portion 222a of dilator 208 is detachably fitted on the vicinity of the opening end of the large-diameter cylindrical portion 220a of trocar tube 207. A proximal end portion of an operation handle 227 is screwed to the outer periphery of the large-diameter cylindrical portion 222a of dilator 208.

A position adjusting mechanism 226 (to be described later) is provided on the small-diameter cylindrical portion 222b of dilator 208. The position adjusting mechanism 226 adjusts the position of the distal end of the trocar needle 206, which projects from the tube 207.

Figure 21:
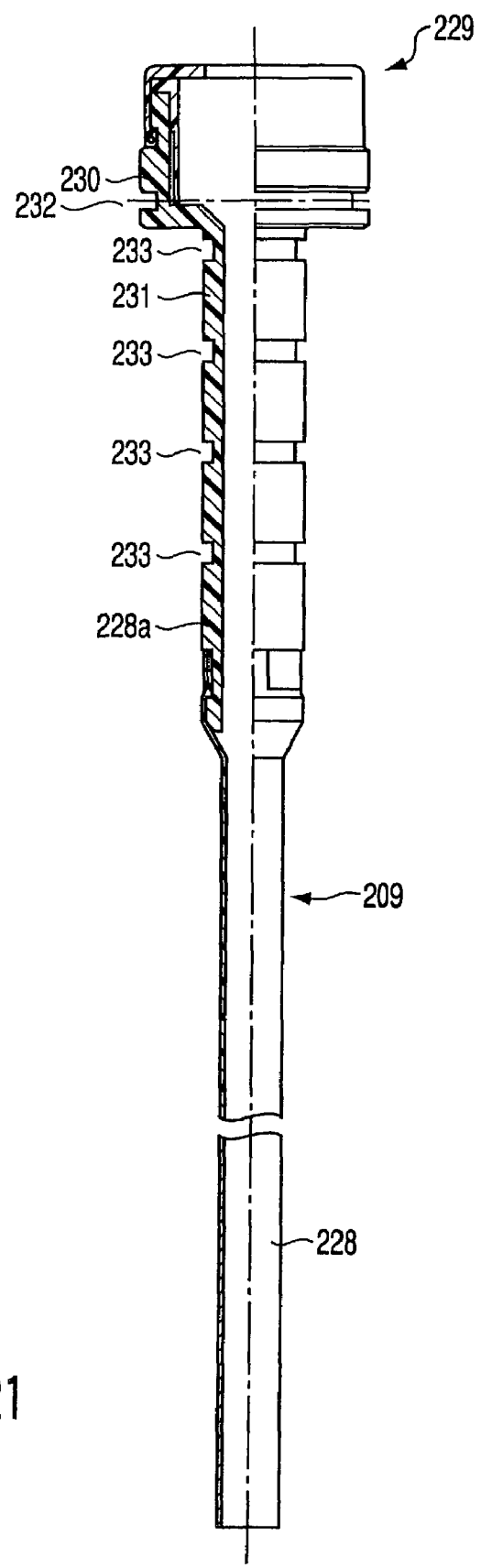
FIG. 21 is a partial cross-sectional side view of the guide member of the ultrasonic trocar according to the sixth embodiment.
Figure 22:
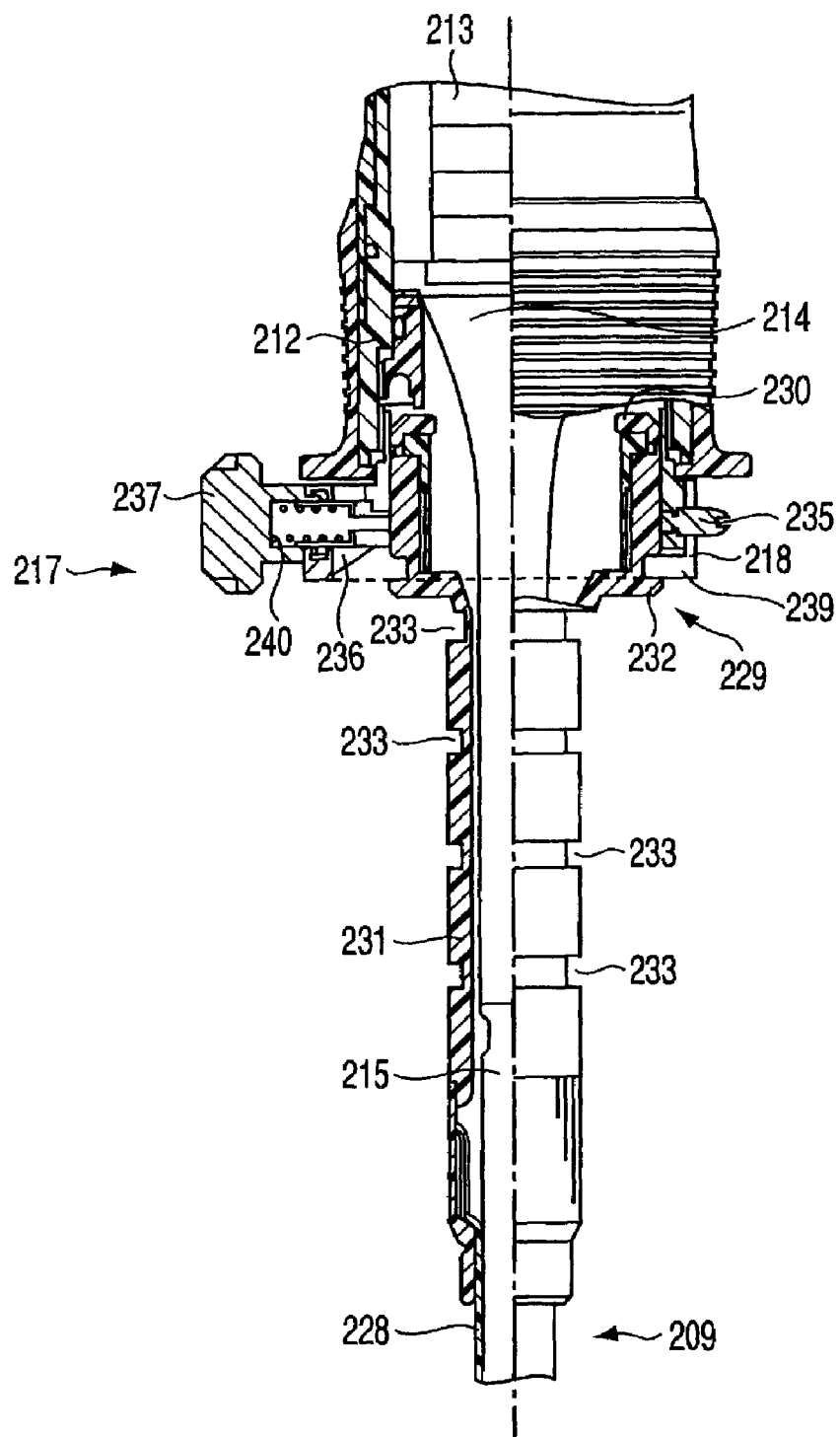
FIG. 22 is a vertical cross-sectional view showing a peripheral structure of a guide member lock mechanism according to the sixth embodiment.

As is shown in FIG. 21, the guide member 209 has a thin straight portion 228. A proximal end portion of the straight portion 228 is provided with a handle section 229. The straight portion 228 is formed of, e.g. Teflon (trademark): PTFE (polytetrafluoroethylene), which is a soft resin material with high heat resistance and smoothness. The straight portion 228 is put in contact with the probe 210 that is oscillated by ultrasonic. For example, even when an inner peripheral surface of a hard metallic pipe is coated with Teflon to form a straight portion 228, the same advantage is obtained as with the resin-made straight portion 228.

The inside diameter of the straight portion 228 is set to be substantially equal to the outside diameter of the pierce needle 216 of trocar needle 206. A proximal end portion of the straight portion 228 is provided with an alignment portion 228a having a diameter substantially equal to the inside diameter of the insertion portion 221 of dilator 208.

The handle section 229 has a large-diameter cylindrical portion 230 and a small-diameter cylindrical portion 231. The large-diameter cylindrical portion 230 is inserted in the guide member lock mechanism 217 of trocar needle 206. The small-diameter cylindrical portion 231 is inserted in the position adjusting mechanism 226 of dilator 208. An annular first engagement groove 232 is formed in the outer periphery of large-diameter cylindrical portion 230. Annular second engagement grooves 233 (four in this embodiment) are formed in the outer periphery of small-diameter cylindrical portion 231 in its axial direction.

Figure 23A:
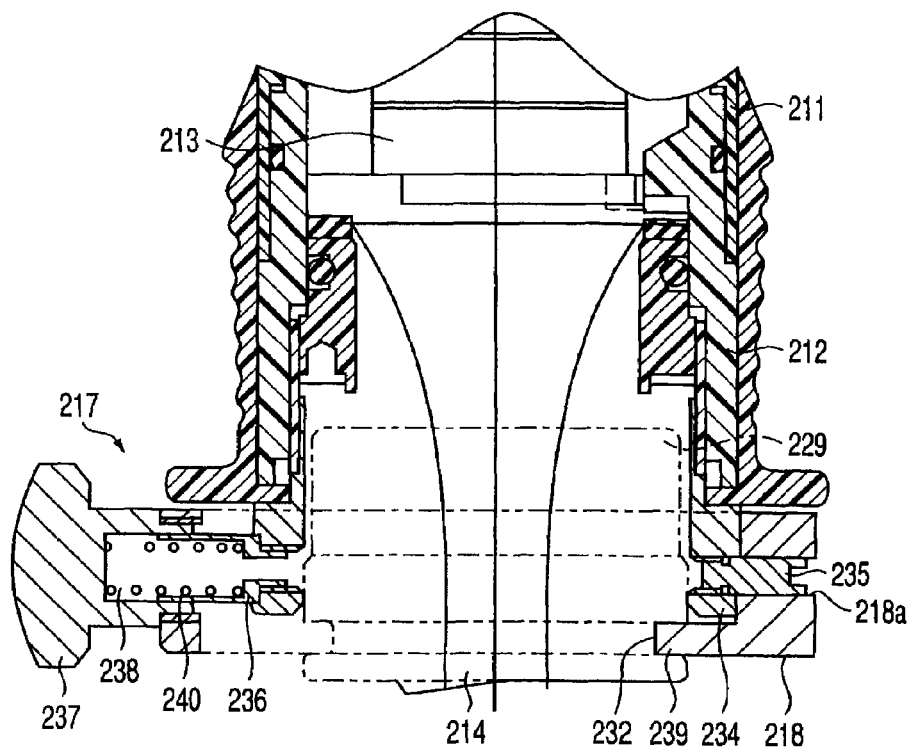
FIG. 23A is a vertical cross-sectional view showing a main part of the guide member lock mechanism according to the sixth embodiment.

As is shown in FIG. 23A, the guide member lock mechanism 217 of trocar needle 206 is provided with a substantially cylindrical lock mechanism support member 234. The support member 234 is coupled to a lower end portion of the housing 212. A guide pin 235 and a cylindrical guide portion 236 are projected from the outer periphery of the support member 234. The guide pin 235 and cylindrical guide portion 236 are disposed opposed to each other at an angular distance of 180° in the circumferential direction of the lock mechanism support member 234.

An annular lock member 218 is provided on the outer periphery of the support member 234. A pin insertion hole 218a, in which the guide pin 235 is axially movably inserted, is formed in the outer periphery of the lock member 218. In addition, a lock button 237 that is projecting is screwed to the outer periphery of lock member 218. The lock button 237 includes an insertion hole 238. The guide portion 236 is axially movably inserted in the insertion hole 238. The lock member 218 is supported to be movable in a direction perpendicular to the axial direction of the trocar needle 206, with the guide pin 235 and guide portion 236 being used as guides.

The lock member 218 has an inwardly projecting engagement claw 239 in the vicinity of the pin insertion hole 218a. The engagement claw 239 is detachably engaged in the first engagement groove 232 of guide member 209. In addition, a compression coil spring 240 is provided within the cylindrical guide portion 236. The spring 240 urges the engagement claw 239 in such a direction as to engage the first engagement groove 232 of guide member 209. When the trocar needle 206 and guide member 209 are assembled, the engagement claw 239 of lock member 218 is locked in the first engagement groove 232 of guide member 209, as shown in FIG. 23A, by the force of the spring 240. In the locked state, if the lock button 237 is pushed against the force of the spring 240, the lock member 218 moves to the right in FIG. 23A. The engagement claw 239 of lock member 218 is then disengaged from the first engagement groove 232 of guide member 209, and the locking is released.

Figure 23B:
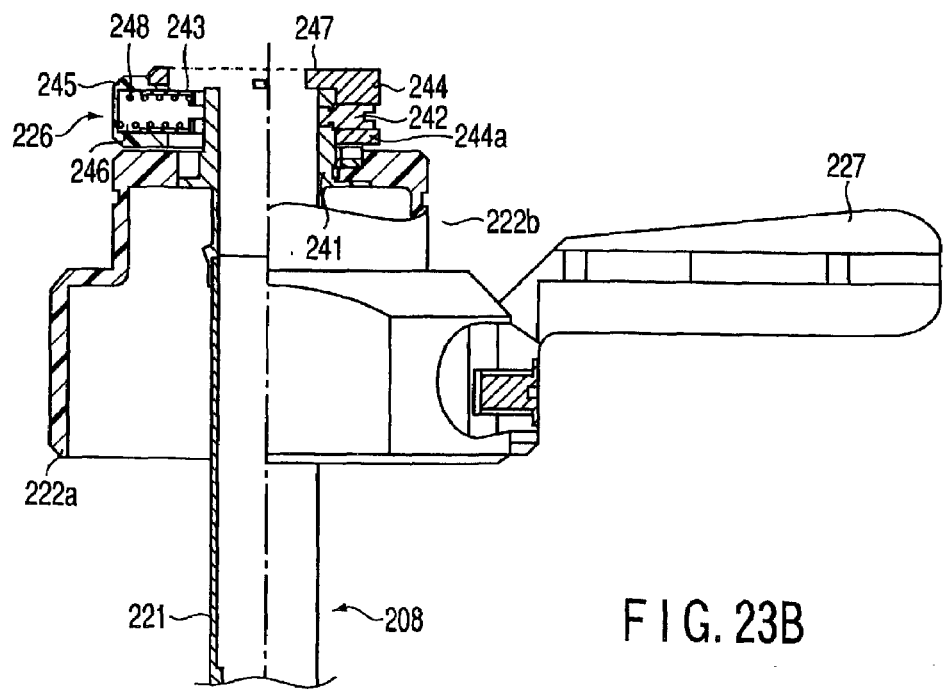
FIG. 23B is a vertical cross-sectional view of a main part of the lock mechanism of the dilator.

In the position adjusting mechanism 226 of dilator 208, as shown in FIG. 23B, a substantially cylindrical lock mechanism support member 241 is projected on the upper side of the small-diameter cylindrical portion 222b. The support member 241 is coupled to the small-diameter cylindrical portion 222b of dilator 208. A guide pin 242 and a cylindrical guide portion 243 are projected from the outer periphery of the support member 241. The guide pin 242 and cylindrical guide portion 243 are disposed opposed to each other at an angular distance of 180° in the circumferential direction of support member 241.

A substantially annular lock member 244 is provided outside the support member 241. A pin insertion hole 244a is formed in the outer periphery of the lock member 244. A guide pin 242 is axially movably inserted in the insertion hole 244a. A lock button (operation portion) 245, which is in a projecting state, is screwed in the pin insertion hole 244a. An insertion hole 246 is formed in the lock button 245. The cylindrical guide portion 243 is axially movably inserted in the insertion hole 246. The lock member 244 is supported to be movable in a direction perpendicular to the axial direction of the trocar needle 206, with the guide pin 242 and cylindrical guide portion 243 being used as guides. As is shown in FIG. 20A, the lock button 245 is disposed opposed to the operation handle 227 of dilator 208 (at an angular distance of 180° ) with respect to the axis of the trocar needle 206.

Figure 24A:
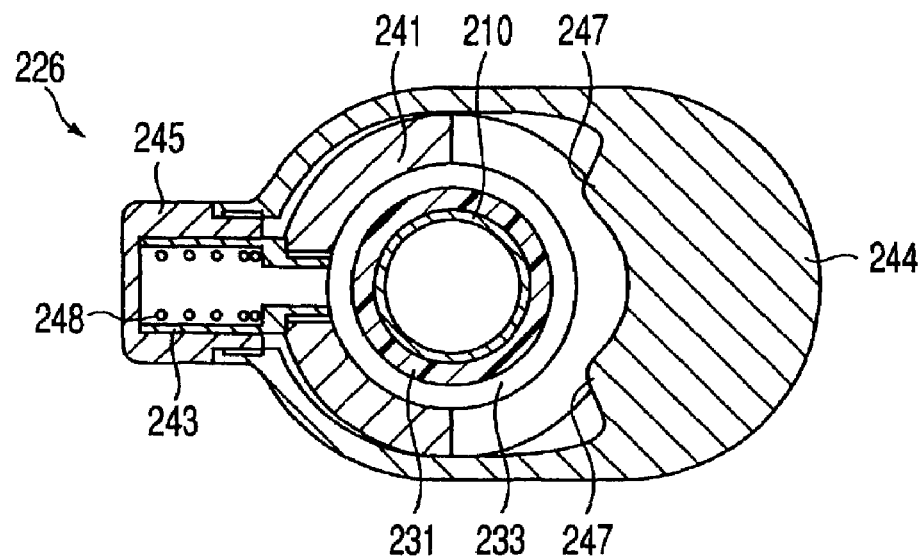
FIG. 24A is a transverse cross-sectional view showing the disengaged state of the lock mechanism of the dilator according to the sixth embodiment.
Figure 24B:
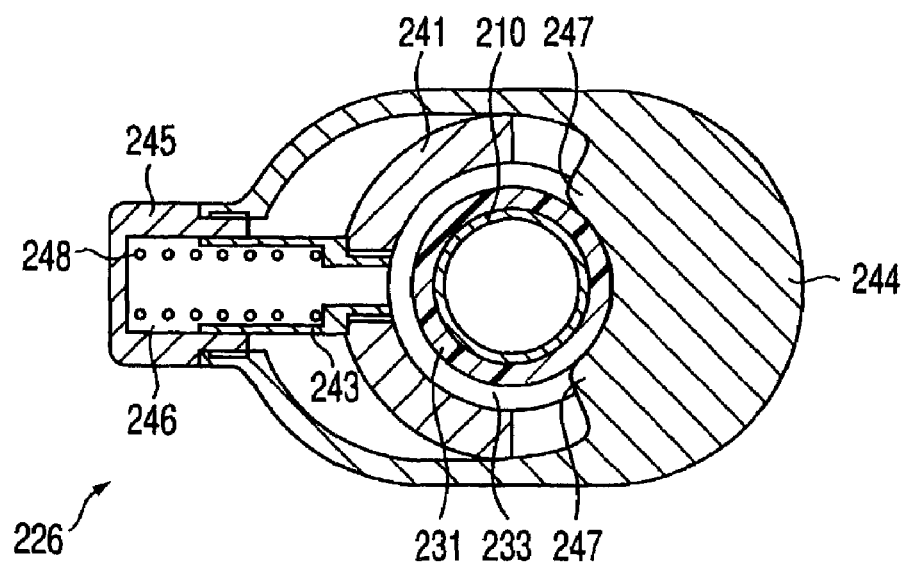
FIG. 24B is a transverse cross-sectional view showing the engaged state of the lock mechanism.

As is shown in FIGS. 24A and 24B, the lock member 244 is provided with two engagement claws 247 projecting inwards in the vicinity of the pin insertion hole 244a. Each engagement claw 247 is detachably engaged with one of the second engagement grooves 233 provided at a given position of guide member 209. A compression coil spring (urging member) 248 is provided within the cylindrical guide portion 243. The spring 248 urges the engagement claws 247 in such a direction as to engage the second engagement groove 233 of guide member 209.

When the dilator 208 and guide member 209 are assembled, as shown in FIG. 24B, the engagement claw 247 of lock member 244 is engaged in the locked state with one of the second engagement grooves 233 of guide member 209 by the force of the spring 248. In the locked state, if the lock button 245 is pushed against the force of the spring 248, the lock member 244 moves to the right in FIG. 24B. Thereby, as shown in FIG. 24A, the engagement claw 247 of lock member 244 is disengaged from the second engagement groove 233 of guide member 209, and the locking is released. If the guide member 209 is axially moved relative to the dilator 208 in the unlocked state, the position of the distal end of the trocar needle 206 projecting from the tube 207 can be adjusted.

Figure 25A:
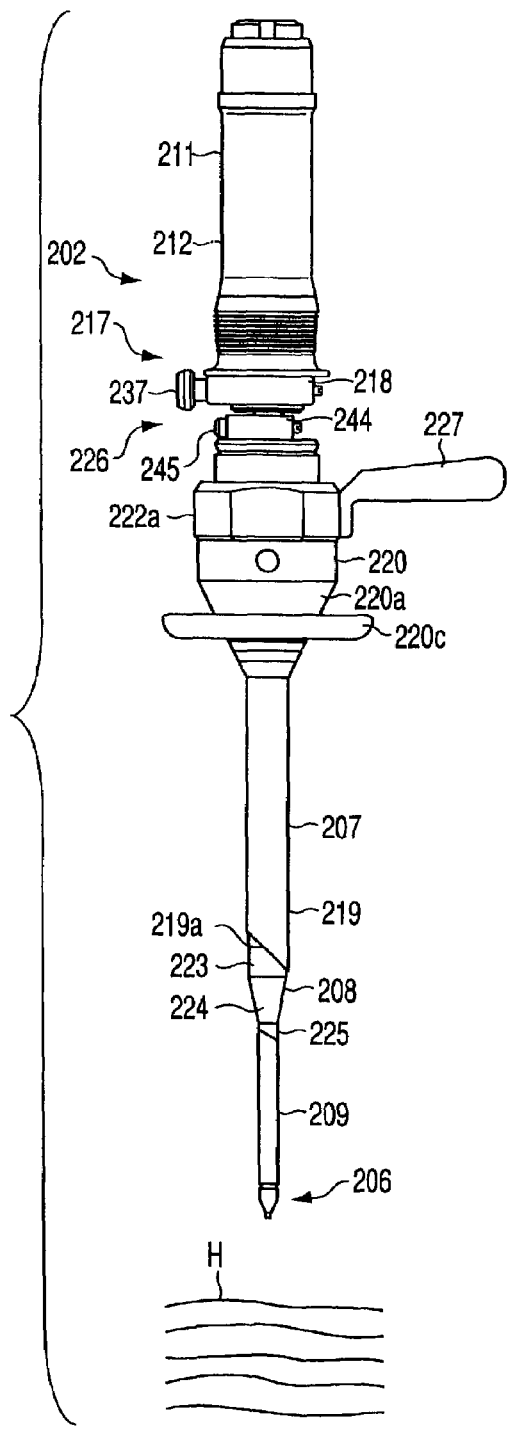
FIG. 25A is a side view showing the length of the distal end portion of the trocar needle according to the sixth embodiment, which is adjusted for a patient whose abdominal wall is thick.
Figure 25B:
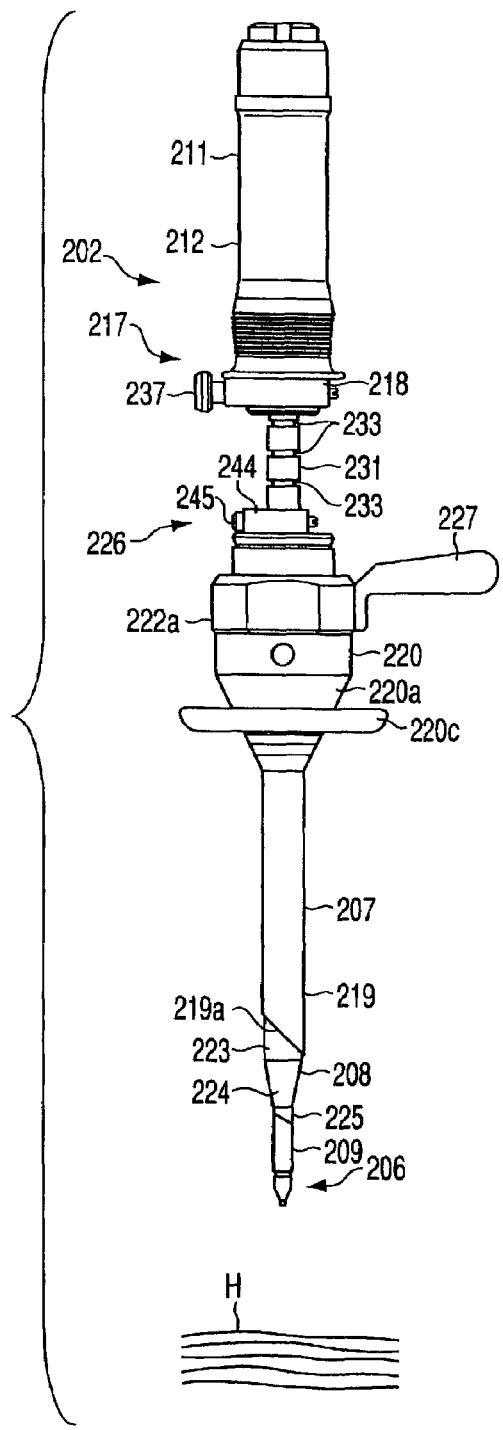
FIG. 25B is a side view showing the length of the distal end portion of the trocar needle, which is adjusted for a patient whose abdominal wall is thin.

For example, if the engagement claw 247 of lock member 244 is adjusted and engaged with the uppermost second engagement groove 233 of guide member 209, the amount of projection of the trocar needle 206 projecting from the tube 207 is increased, as shown in FIG. 25A. On the other hand, if the engagement claw 247 of lock member 244 is adjusted and engaged with the lowermost second engagement groove 233 of guide member 209, the amount of projection of the trocar needle 206 projecting from the tube 207 is decreased, as shown in FIG. 25B.

The operation of the above structure will now be described. When the trocar system 201 of this embodiment is to be used, the handpiece unit 202 of the ultrasonic trocar is, in advance, set in the assembled state, as shown in FIG. 16, in which the trocar needle 206, tube 207, dilator 208 and guide member 209 are combined. At this time, the distal end portion of the straight portion 228 of guide member 209 is projected from the breakage-prevention portion 225 of dilator 208 by a predetermined length, and is kept in this state. In addition, the pierce needle 216 of trocar needle 206 is projected from the distal end of the straight portion 228 of guide member 209 and kept in this state.

When the trocar needle 206 and guide member 209 are assembled, as shown in FIG. 23A, the engagement claw 239 of lock member 218 in the guide member lock mechanism 217 of trocar needle 206 is engaged in the locked state with the first engagement groove 232 of guide member 209.

Furthermore, in this embodiment, the position of the distal end of the needle 206 projecting from the tube 207 can be adjusted by the position adjusting mechanism 226 of dilator 208. In this case, by pushing the lock button 245 of position adjusting mechanism 226 against the force of the spring 248, the lock member 244 moves to the right in FIG. 24B. Thereby, as shown in FIG. 24A, the engagement claw 247 of lock member 244 is disengaged from the second engagement groove 233 of guide member 209, and the locking is released. If the guide member 209 is axially moved relative to the dilator 208 in the unlocked state of the position adjusting mechanism 226 of dilator 208, the position of the distal end of the needle 206 projecting from the tube 207 can be adjusted.

For example, when the patient's abdominal wall H is thick, as shown in FIG. 25A, the engagement claw 247 of lock member 244 is adjusted and engaged with the uppermost second engagement groove 233 of guide member 209. Thereby, the amount of projection of the needle 206 projecting from the tube 207 can be increased. On the other hand, when the patient's abdominal wall H is thin, as shown in FIG. 25B, the engagement claw 247 of lock member 244 is adjusted and engaged with the lowermost second engagement groove 233 of guide member 209. Thereby, the amount of projection of the needle 206 projecting from the tube 207 can be decreased.

The handpiece unit 202, in its assembled state as shown in FIG. 16, is operated so that the trocar tube 207 may pierce and penetrate the patient's skin and body wall and may stay therein. At the time of the piercing operation of the handpiece unit 202, the ultrasonic oscillation device 204 is activated by the operation of the output control device 205. At this time, energy for ultrasonic oscillation is supplied from the ultrasonic oscillation device 204 to the ultrasonic oscillation element 213 of handpiece unit 202 over the connection cable 203. Thus, the ultrasonic oscillation element 213 produces ultrasonic oscillation. The ultrasonic oscillation produced from the ultrasonic oscillation element 213 is amplified by the horn 214 and transmitted to the ultrasonic oscillation transmission rod 215. Thus, the mechanical oscillation of the ultrasonic oscillation element 213 is transmitted to the pierce needle 216 of trocar needle 206 at the distal end of the ultrasonic oscillation transmission rod 215 through the horn 214.

Then, with the handpiece unit 202 being held, the pierce needle 216 of trocar needle 206 is made to pierce the patient's abdominal wall H. At this time, the pierce needle 216 of trocar needle 206 pierces the abdominal wall H in the state in which ultrasonic oscillation is being transmitted to the pierce needle 216 of trocar needle 206. Thus, the pierce needle 216 of trocar needle 206 is made to easily pierce the abdominal wall H with a weak force. With this operation, a small-diameter pierce hole H1 is made in the abdominal wall H.

After the handpiece unit 202 has been inserted up to the location of the breakage-prevention portion 225 near the pierce hole expansion portion 224 of dilator 208, the trocar needle 206 alone is drawn out of the handpiece unit 202. In this state, the handpiece unit 202 is further inserted in the abdominal wall H. Thereby, the diameter of the small-diameter pierce hole made by the trocar needle 206 is increased up to the outside diameter of the tube 207 by means of the conical portion of the pierce hole expansion portion 224 of dilator 208.

Prior to the work for increasing the diameter of the pierce hole, the following operation is performed when the distal end of the guide member 209, which is projected from the distal end of the dilator 208, is in the propinquity of an organ in the abdominal cavity. Specifically, the handle section 229 of guide member 209 is held by the fingers and the handle section 229 of guide member 209 is axially pulled from the dilator 208. Thereby, the amount of projection of the distal end portion of the guide member 209, which projects from the distal end of the dilator 208, is decreased. At this time, the guide member 209 functions as a guide for the insertion of the dilator 208. In general terms, the body wall comprises a plurality of layers. Even if the pierce needle 216 has pierced the body wall, once the pierce needle 216 is pulled out of the body wall, the pierce holes in the respective layers of the body wall are displaced due to muscles. In particular, the peritoneum that is the deepest layer of the body wall may easily be displaced. If the guide member 209 is stayed in the body wall, the axis of insertion of the dilator 208 is guided by the guide member 209 while the pierce hole is being increased. This facilitates the work for increasing the diameter of the pierce hole.

In addition, while the diameter of the pierce hole is being increased, the amount of projection of the distal end portion of guide member 209, which projects from the distal end of dilator 208, is adjusted in accordance with the distance between the organ in the abdominal cavity and the distal end of straight portion 228 of guide member 209. In this work of adjusting the projection amount of guide member 209, the operation of axially pulling the handle section 229 of guide member 209 relative to the dilator 208 and the operation of axially pushing out the handle section 229 are properly combined. Thereby, the amount of projection of the distal end portion of guide member 209, which projects from the distal end of dilator 208, can be adjusted as desired.

When the diameter of the pierce hole is to be increased, the operation of pushing the handpiece unit 202 into the abdominal wall H and the operation of rotating it about the center axis of the trocar tube 207 are simultaneously performed while the operation handle 227 of dilator 208 and the finger hook portion 220c of trocar tube 207 are being held. Thereby, with the operation of pushing the conical portion of the pierce hole expansion portion 224 of dilator 208, the work for increasing the diameter of the small-diameter pierce hole up to the outside diameter of tube 207 is performed. At the time of this work, the insertion portion 219 of trocar tube 207 is successively inserted into the pierce hole that has been enlarged by the pierce hole expansion portion 224 of dilator 208 up to a diameter substantially equal to the diameter of the insertion portion 219 of trocar tube 207. Thus, the insertion portion 219 of trocar tube 207 is inserted in the pierce hole in the abdominal wall H.

When the insertion portion 219 of trocar tube 207 has been inserted in the pierce hole in the abdominal wall H, the pierce hole in the abdominal wall H is dilated by the insertion operation of the insertion portion 219 of trocar tube 207. The insertion portion 219 of trocar tube 207 is relatively firmly fixed in the pierce hole in the abdominal wall H by the elasticity of the peripheral tissue of the pierce hole in the abdominal wall H. In this state, the assembly unit of the dilator 208 and guide member 209 is drawn out of the trocar tube 207. Thus, the trocar tube 207 is inserted and stayed in the pierce hole of abdominal wall H.

With the above structure, the following advantages can be obtained. The trocar system 201 of this embodiment includes the soft cylindrical guide member 209 projected from the distal end of the dilator 208 that is interposed between the tube 207 and trocar needle 206 in the handpiece unit 202 of the ultrasonic trocar. Thus, when the small-diameter pierce hole made by the trocar needle 206 is to be enlarged up to the outside diameter of the tube 207 by the conical portion of the pierce hole expansion portion 224 of dilator 208, the guide member 209 can be put in contact with the organ in the abdominal cavity before the distal end portion of the dilator 208 comes in contact with the organ in the abdominal cavity. Accordingly, during the dilation operation, the distal end portion of dilator 208 is surely prevented from coming in contact with the organ in the abdominal cavity, and the safety in the dilation operation is enhanced.

While the handle section 229 of guide member 209 is being held by the fingers, the operation of axially pulling the handle section 229 of guide member 209 relative to the dilator 208 and the operation of pushing it out are properly combined. Thereby, the amount of projection of the distal end portion of guide member 209, which projects from the distal end of the dilator 208, can be desirably adjusted. Accordingly, the amount of projection of the distal end portion of guide member 209 can be desirably adjusted in accordance with conditions such as the thickness of the abdominal wall H that is to be pierced by the trocar tube 207, or the distance from the organ. As a result, the organ in the abdominal cavity will never be pressed during the dilation operation for increasing the diameter of the small-diameter pierce hole made in the abdominal wall H by the trocar needle 206 up to the outside diameter of tube 207. Moreover, the work for inserting and staying the tube 207 in the abdominal wall H can be carried out easily and quickly.

The straight breakage-prevention portion 225 is provided at the distal conical end portion of the pierce hole expansion portion 224 of dilator 208. Thus, when a lateral force acts on the soft guide member 209 projecting from the distal end of dilator 208, the force acting in such a direction as to bend the guide member 209 at the distal conical portion of the pierce hole expansion hole 224 of dilator 208 can be dispersed over the wide area of the straight breakage-prevention section 225 of dilator 208. Accordingly, the conical distal portion of the pierce hole expansion portion 224 of dilator 208 is prevented from exerting a large local bending force to the guide member 209, and the guide member 209 is protected against bending. During the dilation operation, the breakage-prevention portion 225 of dilator 208 can be made to function also as the guide member for the dilation work. Thus, the operability of the dilation work of dilator 208 can be enhanced.

In this embodiment, as shown in FIG. 23A, the guide member lock mechanism 217 of handpiece unit 202 engages the guide member 209 in the locked state in which the engagement claw 239 of lock member 218 engages the first engagement groove 232 of guide member 209. Thus, the relative position of the guide member 209 and trocar needle 206 is fixed at the set position. As a result, when the needle 206 is made to pierce the patient's body wall, the proximal end portion of tube 207 is never disengaged from the proximal end portion of the trocar needle 206. Unlike the prior art, the operation of the trocar does not become unstable.

Furthermore, the position of the distal end of trocar needle 206 projecting from the tube 207 can be adjusted, before insertion in the body wall, by the position adjusting mechanism 226. The amount of insertion of the distal end portion of the trocar needle 206 is adjusted, as desired, in accordance with conditions such as the thickness of the body wall for piercing or the location of piercing. Compared to the prior art, the needle can be made to pierce the patient's body wall more efficiently in a shorter time period.

In this embodiment, as shown in FIG. 20A, the lock button 245 of position adjusting mechanism 226 of dilator 208 is disposed opposed to the operation handle 227 of dilator 208 (at an angular distance of 180°) with respect to the center axis of the trocar needle 206. Thus, the lock button 245 is easy to handle.

Figure 26:
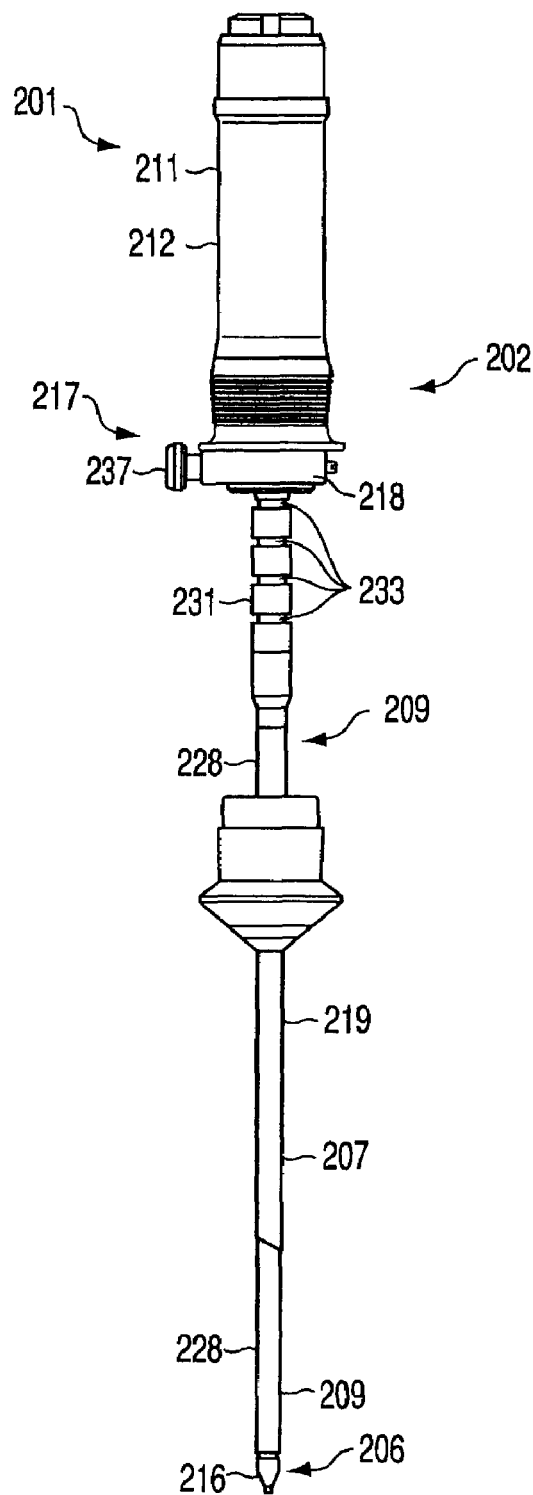
FIG. 26 is a side view showing a state in which a trocar needle of an ultrasonic trocar according to a seventh embodiment of the invention is inserted in a small-diameter tube.

FIG. 26 shows a seventh embodiment of the present invention. This embodiment is made by altering the structure of the handpiece unit 202 of the sixth embodiment (see FIGS. 16 to 25) in the following fashion. Except for the altered portions, the handpiece unit 202 has the same structure as that in the sixth embodiment and a description thereof is omitted.

Specifically, in this embodiment, the tube 207 has an insertion portion 219 having a relatively small diameter (e.g. about 5 mm) and a short length. The inside diameter of the insertion portion 219 of tube 207 is set to be substantially equal to, for example, the outside diameter of the straight portion 228 of guide member 209. In this embodiment, the dilator 208 of the sixth embodiment is omitted. The straight portion 228 of the guide member 209 is directly inserted in the insertion portion 219 of tube 207.

In this embodiment, the guide member lock mechanism 217 of handpiece unit 202 engages the guide member 209 in the locked state in which the engagement claw 239 of lock member 218 engages the first engagement groove 232 of guide member 209. Thus, the relative position of the guide member 209 and trocar needle 206 is fixed at the set position. As a result, when the needle 206 is made to pierce the patient's body wall, the proximal end portion of tube 207 is never disengaged from the proximal end portion of the trocar needle 206. Unlike the prior art, the operation of the trocar does not become unstable.

Figure 27:
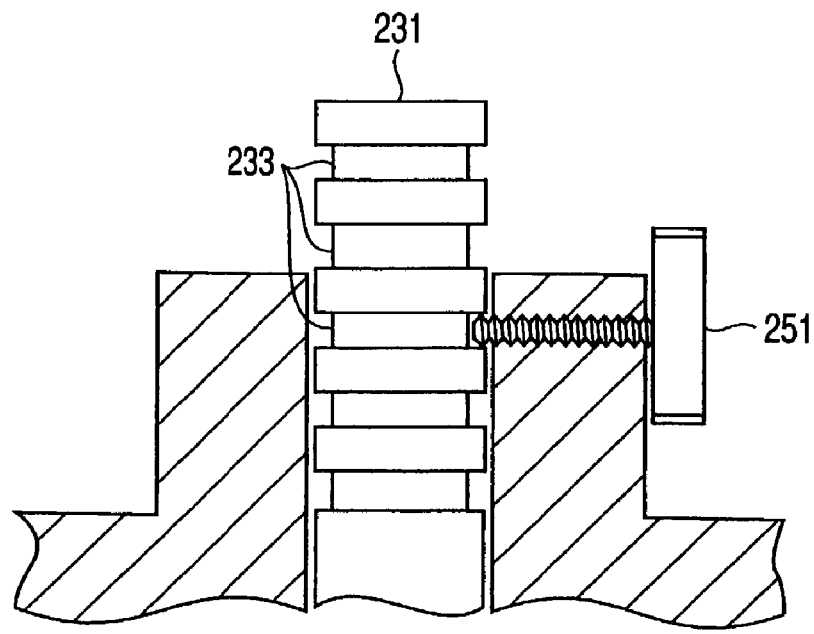
FIG. 27 is a vertical cross-sectional view showing a main part of a first modification of the lock mechanism of the dilator according to the sixth embodiment.
Figure 28A:
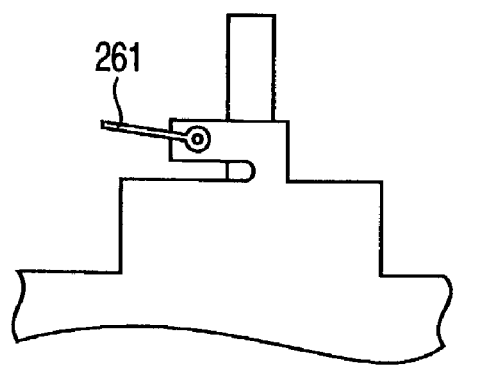
FIG. 28A is a side view showing a second modification of the lock mechanism of the dilator of the sixth embodiment.
Figure 28B:
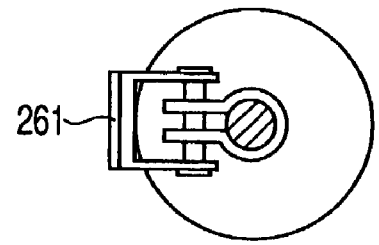
FIG. 28B is a plan view of the lock mechanism.

The present invention is not limited to the above embodiments. For example, as shown in FIG. 27 as a first modification of the guide member lock mechanism 217 of the sixth embodiment, a fixing screw member 251 can detachably be engaged in the second engagement groove 233 in the outer periphery of the small-diameter cylindrical portion 231. In addition, as shown in FIGS. 28A and 28B as a second modification, a lock mechanism using an operation lever 261 may be provided.

Needless to say, other modifications may be made without departing from the spirit of the present invention.

The present invention can provide a trocar and a trocar system wherein a tube for piercing in a patient's body can be easily and quickly inserted and stayed in the patient's skin and body wall.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A trocar system comprising:
a trocar needle structured to pierce a body wall;
an outer tube including a distal end and a proximal end from which the trocar needle is insertable;
a dilator which is interposed between the outer tube and the trocar needle, after being inserted from the proximal end of the outer tube, and has a pierce hole expansion portion that dilates a small-diameter pierce hole made by the trocar needle;
a guide member which includes a cylindrical portion which is projected outward from a distal end portion of the dilator, after being inserted from a proximal end portion of the dilator, the guide member including a handle portion which projects from a proximal end of the dilator, with the guide member engaged with the dilator; and
an adjusting mechanism for changing an amount of projection of the cylindrical portion by relatively moving the guide member and the dilator according to an operation of the handle portion to change the amount of projection of the cylindrical portion in a state in which the guide member and the dilator are combined.

2. A trocar system according to claim 1, wherein the dilator has a straight breakage-prevention portion at a conical distal end portion of the pierce hole expansion portion.

3. A trocar system according to claim 1, including an oscillator element operative for producing ultrasonic oscillation coupled to said trocar needle, thereby making the trocar needle capable to pierce an abdominal cavity wall.

4. A trocar system comprising:
a needle structured to pierce and to be inserted into a body wall;
an oscillation element which produces ultrasonic oscillation and is connected to the needle;
a sheath including a proximal end from which the needle is insertable, and a distal end which has a first opening from which the needle is projectable;
a trocar tube in which the sheath is insertable and which has a second opening at a distal end portion thereof, from which the distal end portion of the sheath is projectable, a length of the sheath projecting from the distal end portion of the trocar tube being greater than a thickness of the body wall; and
an adjusting mechanism in which a length of the sheath projecting from the distal end portion of the trocar tube is changed by an operation of the proximal end of the sheath according to a condition of a pierced portion, and the sheath is fixable, with the length changed,
wherein the sheath is projected from the proximal end of the trocar tube, while being engaged with the trocar tube.

5. A trocar system according to claim 4, further comprising a dilator in which the sheath is insertable and which has a third opening at a distal end portion thereof, from which the sheath is projectable, said dilator being insertable in the trocar tube, and the distal end portion of the dilator being projectable from said second opening.

6. A trocar system according to claim 5, wherein the distal end portion of the dilator has an expansion portion which dilates a hole formed in the body wall by the needle.

7. A trocar system according to claim 6, wherein the expansion portion has a distal end portion and a proximal end portion, and an outside diameter of the distal end portion is less than an outside diameter of the proximal end portion.

8. A trocar system according to claim 6, wherein the expansion portion has a substantially conical shape, and has an outside diameter gradually decreasing toward the distal end portion thereof.

9. A trocar system according to claim 6, further comprising an auxiliary member provided at a distal end portion of the expansion portion in order to prevent bending of the projection portion of the sheath.

10. A trocar system according to claim 8, wherein the auxiliary member is a hollow member having a tube path in the inside thereof, and the tube path of the auxiliary member communicates with a tube path of the dilator in which the sheath is inserted.

11. A trocar system according to claim 8, wherein a face of a distal end portion of the auxiliary member, which includes an opening, is inclined with respect to a longitudinal axis of the dilator.

12. The trocar according to claim 5, wherein the adjusting mechanism is provided in the dilator.

13. A trocar system according to claim 4, wherein a face of a distal end portion of the trocar tube, which includes said second opening, is inclined with respect to a longitudinal axis of the trocar tube.

14. A trocar comprising:
a needle structured to pierce and to be inserted into a body wall;
an oscillation element including a proximal end and a distal end to which the needle is connected, the oscillation element being configured to transmit ultrasonic oscillation to the needle;
a holding member including a distal end and a proximal end fixed to the proximal end of the oscillation element to hold the oscillation element;
a first tube including a handle portion, a distal end and a proximal end from which the needle is insertable, the first tube defining a position of part of the needle which is projected from the distal end of the first tube, proximal end of the first tube and the distal end of the holding member are engaged with each other, with the needle inserted from the distal end of the first tube; and
a second tube including a proximal end from which the first tube is insertable, and from which the handle portion of the first tube projects, and a distal end from which the distal end of the first tube is projectable in accordance with the relative movement between the first tube and the second tube, which is carried out by an operation of the handle portion of the first tube after the first tube is inserted from the proximal end of the second tube.

15. A trocar comprising:
a needle structured to pierce and to be inserted into a body wall;
an oscillation element to which the needle is connected, and which is configured to transmit ultrasonic oscillation to a distal end of the needle;
a first tube including a handle portion, a distal end and a proximal end from which the needle is insertable, the first tube being fixable, with a distal end of the needle projecting from the distal end of the first tube;
a second tube including a proximal end in which the first tube and the needle are insertable, and from which the handle portion of the first tube projects and a distal end from which the distal end of the first tube and the needle are projectable;
a lock mechanism for fixing the first tube to the second tube in one of at least two positions, which is selected in accordance with the movement of the first tube relative to the second tube by an operation of the handle portion, the lock mechanism enabling adjusting an amount of projection of the distal end of the first tube from the distal end of the second tube by changing a position of the first tube with respect to the second tube to said selected one of said at least two positions.

16. A trocar according to claim 15, further comprising:
a dilator which is insertable in the second tube and in which the first tube is insertable; and
wherein the dilator comprises an expansion portion projecting from the distal end portion of the second tube in the state in which the dilator is inserted in the second tube, and which dilates a hole formed in the body wall by the needle.

17. A trocar according to claim 16, wherein the expansion portion has a distal end portion and a proximal end portion, and an outside diameter of the distal end portion is less than an outside diameter of the proximal end portion.

18. A trocar according to claim 16, wherein the expansion portion has a substantially conical shape, and has an outside diameter gradually decreasing toward the distal end portion thereof.

19. A trocar according to claim 16, further comprising an auxiliary member provided at a distal end portion of the expansion portion in order to prevent bending of part of the first tube, which is projected from the distal end of the second tube.

20. A trocar according to claim 19, wherein said auxiliary member is a hollow member having a tube path in the inside thereof, and the tube path of the auxiliary member communicates with a tube path of the second tube in which the first tube is inserted.

21. A trocar according to claim 19, wherein a face of a distal end portion of the auxiliary member, which includes an opening, is inclined with respect to a longitudinal axis of the second tube.

22. The trocar according to claim 16, wherein
the lock mechanism also fixes relative movement of the first tube and the dilator, and is configured to change the amount of projection of the first tube projecting from the distal end of the second tube by relatively moving the first tube and the dilator, and to fix the changed state thereof by fixing the first tube with respect to the dilator, in a state in which the first tube, in which the needle is fixed, is inserted in the dilator which is inserted into the second tube.

23. The trocar according to claim 16, wherein the lock mechanism is provided in the dilator.

24. A trocar according to claim 15, wherein a face of a distal end portion of the second tube which includes an opening, is inclined with respect to a longitudinal axis of the second tube.

25. The trocar according to claim 15, wherein the lock mechanism is configured to change the amount of projection of the first tube with respect to the distal end of the second tube in accordance with a condition of a piercing portion.

26. The trocar according to claim 15, farther comprising:
a needle fixing mechanism for fixing the needle and the first tube in a state in which the needle projects from the distal end of the first tube.

27. A trocar system according to claim 15, wherein the lock mechanism comprises a plurality of groove portions formed in the second tube and a projection member provided on the first tube.

* * * * *